United States Patent [19]

Moriyasu et al.

[11] Patent Number: 5,123,954
[45] Date of Patent: Jun. 23, 1992

[54] 3,4-TRANS-4-ETHYL-1-(SUBSTITUTED PHENYL)-3-(SUBSTITUTED PHENYL) PYRROLIDIN-2-ONES, METHOD FOR PREPARING THE SAME, AND HERBICIDAL METHOD COMPOSITIONS CONTAINING THE SAME AS HERBICIDALLY ACTIVE INGREDIENTS

[75] Inventors: Koichi Moriyasu, Mobara; Kengo Oda, Hiratsuka; Kanji Tomiya, Mobara; Tohru Miura, Mobara; Makoto Nishida, Mobara; Sachiko Hibi, Mobara, all of Japan

[73] Assignee: Mitsui Toatsu Chemicals Incorporated, Tokyo, Japan

[21] Appl. No.: 755,366

[22] Filed: Sep. 6, 1991

[30] Foreign Application Priority Data

Sep. 7, 1990 [JP] Japan .................. 2-235765
Mar. 8, 1991 [JP] Japan .................. 3-043197

[51] Int. Cl.$^5$ .................. C07D 207/34; A01N 43/36
[52] U.S. Cl. .................. 71/95; 548/543
[58] Field of Search .................. 548/543; 71/95

[56] References Cited

U.S. PATENT DOCUMENTS 4,069,038 1/1978 Teach .................. 548/543
4,960,457 10/1990 Wollard .................. 548/543

FOREIGN PATENT DOCUMENTS 0055215 6/1982 European Pat. Off. .
0387869 9/1990 European Pat. Off. ............ 548/543

Primary Examiner—David B. Springer
Attorney, Agent, or Firm—Millen, White & Zelano

[57] ABSTRACT

A 3,4-cis isomer of 4-ethyl-1-(substituted phenyl)-3-substituted phenyl)pyrrolidin-2-one, when reacted with a base, can be effectively convered into a 3,4-trans isomer thereof which has a high herbicidal activity useful as an effective ingredient for a herbicidal composition. Furthermore, 3,4-trans-4-ethyl-1-(substituted phenyl)-3-(substituted phenyl)pyrrolidin-2-one compounds represented by the formula (III)

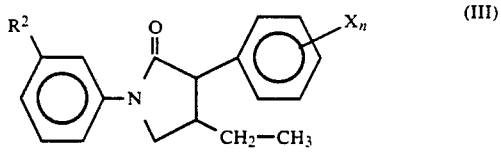

(wherein $R^2$ is an isopropyl group, and X is a fluorine atom, chlorine atom or bromine atom substituted at the 3-position, or fluorine atoms substituted at the 3- and 4-positions or the 3- and 5-positions) have an extremely excellent activity particularly as a herbicidally active ingredient of the herbicidal composition for rice paddy fields.

20 Claims, No Drawings

3,4-TRANS-4-ETHYL-1-(SUBSTITUTED PHENYL)-3-(SUBSTITUTED PHENYL) PYRROLIDIN-2-ONES, METHOD FOR PREPARING THE SAME, AND HERBICIDAL METHOD COMPOSITIONS CONTAINING THE SAME AS HERBICIDALLY ACTIVE INGREDIENTS

BACKGROUND OF THE INVENTION (i) Field of the Invention

The present invention relates to 3,4-trans-4-ethyl-1-(substituted phenyl)-3-(substituted phenyl)pyrrolidin-2-ones, a method for preparing the same, and herbicidal compositions for paddy fields containing the same as herbicidally active ingredients.

(ii) Description of the Prior Art

It has already been disclosed that certain kinds of pyrrolidin-2-one derivatives have a herbicidal activity, and the description regarding this fact is made in U.S. Pat. Nos. 4,110,105, 4,210,589 and 4,874,422, E.P. Publication No. 387,869 and the like. Furthermore, 3-chloro-4-chloromethyl-1-(3-trifluoromethylphenyl)-2-pyrrolidinone (general name fluorochloridone) which is a typical compound in these publications is commercially available. Additionally, also in U.S. Pat. No. 4,960,457, pyrrolidinone derivatives and herbicidal compositions are disclosed.

When utilized as herbicidal compositions, compounds disclosed in the above-mentioned U.S. Pat. Nos. 4,110,105, 4,210,589 and 4,874,422 are required to be used in a relatively large amount, i.e., in a relatively high application rate. In particular, when these compounds are used in paddy fields, there is the problem that they have a pharmaceutically injurious action on rice plants which are useful crops.

Moreover, compounds disclosed in examples of E.P. Publication No. 387,869 or U.S. Pat. No. 4,960,457 have the problem that an effect to weeds in a growing period is low, when they are used in paddy fields.

Heretofore, there has not been known any method for selectively and effectivel.y preparing preferable isomers of these pyrrolidinone derivatives which have a herbicidal activity, i.e., 3,4-trans isomers. Therefore, it has been very difficult to apply these compounds as practical herbicidal compositions.

SUMMARY OF THE INVENTION

The present invention has been developed in view of the various problems of the above-mentioned conventional 2-pyrrolidinone derivatives.

Thus, an object of the present invention is to provide a method for preparing an isomer having a preferable activity as an effective ingredient of a herbicidal composition, i.e., a 3,4-trans isomer selectively and effectively.

Another object of the present invention is to provide a selective herbicidal composition which have no injurious action on rice plants in paddy fields, is effective in a low application rate, and can be used in a prolonged term of from the pre-emergence of weeds to the growing period of the emerged weeds.

In order to achieve these objects, the present inventors have intensively investigated on a technique for effectively preparing a trans isomer having a high activity, and as a result, they have found that when a base is reacted with a cis isomer, the trans isomer can be obtained. Additionally, it has also be found that some compounds of the trans isomers are much more excellent as herbicidal compositions, as compared with the other compounds thereof and what is better, they have no injurious action on rice plants which are useful crops. In consequence, the present invention has been achieved on the basis of this knowledge.

According to the present invention, there can be provided a method for effectively preparing 3,4-trans-4-ethyl-1-(substituted phenyl)-3-(substituted phenyl)pyrrolidin-2-ones which are useful as an effective ingredient of a herbicidal composition. The herbicidal compositions containing 3,4-trans-4-ethyl-1-(substituted phenyl)-3-(substituted phenyl)pyrrolidin-2-one derivatives, above all, 3,4-trans-4-ethyl-3-(substituted phenyl)-1-(3-isopropylphenyl)pyrrolidin-2-one derivatives exert a herbicidal activity to various troublesome weeds in paddy fields in a low application rate in the term of from the pre-emergence of the weeds to the growing period of the emerged weeds. In addition, these herbicidal compositions have excellent selectivity to the rice plants, and so they can be used safely.

DETAILED DESCRIPTION OF THE PREFERRED EMBODIMENTS

A method for preparing a 3,4-trans isomer of 4-ethyl-1-(substituted phenyl)-3-(substituted phenyl)pyrrolidin-2-ones having structures represented by the formula (I)

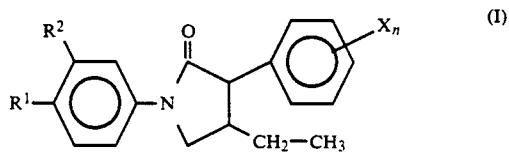

(wherein $R^1$ is a hydrogen atom, halogen atom or methyl group; $R^2$ is a trifluoromethyl group, haloalkoxy group having 1 to 3 carbon atoms, haloalkylthio group having 1 to 3 carbon atoms; lower alkyl group having 1 to 4 carbon atoms, alkoxy group having 1 to 4 carbon atoms, nitro group, cyano group, phenoxy group, hydroxyl group or halogen atom; X is a hydrogen atom, halogen atom, trifluoromethyl group, alkyl group having 1 to 3 carbon atoms, cyano group or nitro group; and n is 1 or 2 and denotes the number of the substituents represented by X, and in the case of n=2, the groups of X may be identical or different) of the present invention comprises the step of reacting a base with a 3,4-cis isomer of 4-ethyl-1-(substituted phenyl)-3-(substituted phenyl)pyrrolidin-2-ones having the structures represented by the formula (I).

The 3,4-trans isomer of 4-ethyl-1-(substituted phenyl)-3-(substituted phenyl)pyrrolidin-2-ones of the present invention can be represented by the formula (III)

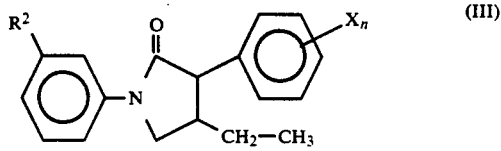

(wherein $R^2$ is an isopropyl group, and X is a fluorine atom, chlorine atom or bromine atom substituted at the 3-position, or fluorine atoms substituted at the 3- and 4-positions or the 3- and 5-positions).

The herbicidal composition for paddy fields of the present invention contains the 3,4-trans isomer of 4-ethyl-1-(substituted phenyl)-3-(substituted phenyl)pyrrolidin-2-ones represented by the formula (III) as a herbicidally active ingredient.

The preparation method of the present invention is directed to a method for preparing a 3,4-trans isomer of 4-ethyl-1-(substituted phenyl)-3-(substituted phenyl)-pyrrolidin-2-ones of the formula (I) in a high yield and a high selectivity by reacting a base with either a 3,4-cis isomer or a mixture of the 3,4-trans isomer and 3,4-cis isomer of 4-ethyl-1-(substituted phenyl)-3-(substituted phenyl)pyrrolidin-2-ones of the formula (I).

In the preparation method of the present invention, the employment of the base is essential.

Examples of the usable base include hydroxides of alkaline metals such as sodium hydroxide, potassium hydroxide and lithium hydroxide, hydroxides of alkaline earth metals such as calcium hydroxide and barium hydroxide, sodium salts of inorganic acids such as sodium carbonate, sodium hydrogencarbonate, sodium phosphate, sodium hydrogenphosphate, sodium sulfite, sodium hydrogensulfite, sodium nitrite, sodium hypochlorite, sodium cyanide and sodium phosphinate, potassium salts of inorganic acids such as potassium carbonate, potassium hydrogencarbonate, potassium phosphate, potassium hydrogenphosphate, potassium sulfite, potassium hydrogensulfite, potassium nitrite, potassium hypochlorite, potassium cyanide and potassium phosphinate, lithium salts of inorganic acids, alkaline metals such as metallic sodium and metallic potassium, metallic hydrides such as sodium hydride, diisobutylaluminum hydride, aluminumlithium hydride, aluminumsodium hydride, borolithium hydride and borosodium hydride, alcoholates such as t-butoxypotassium and sodium methoxide, phenolates, ammonia, sodium salts of carboxylic acids such as sodium acetate, sodium formate, sodium oxalate and sodium benzoate, potassium salts of carboxylic acids such as potassium acetate, potassium formate, potassium oxalate and potassium benzoate, aliphatic amines such as methylamine, ethylamine, dimethylamine, diethylamine and triethylamine, aromatic amines such as aniline and N,N-dimethylaniline, organic bases such as pyridine, picoline, quinoline, 1,8-diazabicyclo(5.4.0)undec-7-ene (DBU), crown ethers, basic ion exchange resins, and mixtures thereof. Among these compounds, preferable are inexpensive sodium hydroxide, potassium hydroxide, potassium carbonate, sodium hydride and 1,8-diazabicyclo(5.4.0)-undec-7-ene (DBU).

The amount of the base depends upon the kind of selected base, but it is usually in the range of from 0.001 to 10 equivalents, preferably from 0.01 to 3 equivalents based on 1 equivalent of a 4-ethyl-1-(substituted phenyl)-3-(substituted phenyl)pyrrolidin-2-one.

A temperature at which the base is reacted depends upon the kind of selected base, but it is usually in the range of from 0° to 200° C., preferably from room temperature to 100° C.

The reaction can be carried out, if necessary, under reduced pressure or increased pressure, but such pressure conditions have no merit. Usually, the reaction is done under atmospheric pressure.

In the preparation method of the present invention, a solvent is usually used. No particular restriction is put on the kind of solvent, so long as it does not have a bad influence on the reaction. Examples of the usable solvent include water, alcohols such as methanol, ethanol, isopropanol and ethylene glycol, ethers such as diethyl ether, tetrahydrofuran, ethylene glycol dimethyl ether and diethylene glycol dimethyl ether, a nitrile such as acetonitrile, a ketone such as acetone, esters such as ethyl acetate and n-butyl acetate, a hydrocarbon such as n-hexane, halogenated hydrocarbons such as methylene chloride, chloroform and 1,2-dichloroethane, aromatic hydrocarbons such as benzene, toluene, xylene and cumene, non-protonic polar solvents such as N,N-dimethylformamide, 1,3-dimethyl-2-imidazolizinone, sulforane, DMSO, DMAc and HMPA, and mixtures thereof.

The amount of the solvent is usually in the range of from 0.3 to 30 parts by weight, preferably from 1 to 10 parts by weight based on 1 parts by weight of a 4-ethyl-1-(substituted phenyl)-3-(substituted phenyl)pyrrolidin-2-one.

For the preparation of the cis isomer or the mixture of the cis isomer and the trans isomer of 4-ethyl-1-(substituted phenyl)-3-(substituted phenyl)pyrrolidin-2-ones which can be used as the starting material in the preparation method of the present invention, there are various techniques, and for example, the following methods (1) and (2) are useful.

(1) Cyclizing reaction of an N-(2-butenyl)-N-(substituted phenyl)-2-halo-2-(substituted phenyl)-acetamide by reduction.

A cyclizing agent which is effective in this cyclizing reaction is a trialkyltin hydride typified by tributyltin hydride, and in general, the cyclizing reaction is carried out in an aromatic solvent such as benzene, toluene or xylene. A reaction temperature is preferably from 50° to 140° C., more preferably from 60° to 90° C. The reaction proceeds by adding a catalytic amount of a radical generator such as α,α-azobisisobutyronitrile or benzoyl peroxide to a reaction mixture. The irradiation of light is also an effective means for allowing the reaction to proceed.

An N-(2-butenyl)-N-(substituted phenyl)-2-halo-2-(substituted phenyl)acetamide can be easily obtained by reacting N-(2-butenyl)aniline with an α-halo-phenylacetic acid halide.

This reaction is carried out in the absence of any solvent or in an inert solvent, and examples of the inert solvent include aromatic solvents such as benzene, toluene, xylene, chlorobenzene and dichlorobenzene, halogenated hydrocarbons such as methylene chloride, chloroform and 1,2-dichloroethane, ethers such as diethyl ether, tetrahydrofuran, ethylene glycol dimethyl ether, diethylene glycol dimethyl ether and dioxane, a nitrile such as acetonitrile, a ketone such as acetone, esters such as ethyl acetate and n-butyl acetate, a hydrocarbon such as n-hexane, and non-protonic polar solvents such as N,N-dimethylformamide, 1,3-dimethyl-2-imidazolizinone, sulforane, DMSO, DMAc and HMPA. The reaction can proceed at an optional temperature, for example from −20° to 140° C., and this reaction may be carried out in the presence of a base such as triethylamine, pyridine, N,N-dimethylaniline, sodium hydride, potassium hydride, sodium carbonate, potassium carbonate and sodium hydrogencarbonate.

N-(2-butenyl)aniline can be prepared by a method described in U.S. Pat. No. 4,132,713, and the α-halo-phenylacetic acid halide can be prepared from a mandelic acid derivative or a phenylacetic acid by a known process.

(2) The 4-ethyl-1-(substituted phenyl)-3-(substituted phenyl)pyrrolidin-2-one can also be prepared by the dehalogenation of a 4-(o-haloethyl)-1-(substituted phenyl)-3-(substituted phenyl)pyrrolidin-2-one which can be obtained by cyclizing an N-(2-butenyl)-N-(substituted phenyl)-2-halo-2-(substituted phenyl)acetamide in the presence of a transition metal catalyst.

The thus obtained 4-ethyl-1-(substituted phenyl)-3-(substituted phenyl)pyrrolidin-2-one is a mixture of a trans isomer and a cis isomer regarding a steric conformation at the 3- and 4-positions of a pyrrolidine ring.

With regard to the 3,4-cis-4-ethyl-1-(substituted phenyl)-3-(substituted phenyl)pyrrolidin-2-one which can be used as the raw material in the method of the present invention, the isolated cis isomer, needless to say, can be used, and a mixture of the cis isomer and the trans isomer may be used. The base can be added either directly to the reaction mixture including the cisisomer obtained through the preparation process of the cis-isomer or to a product obtained through an aftertreatment of the reaction mixture.

The 3,4-trans-4-ethyl-1-(substituted phenyl)-3-(substituted phenyl)pyrrolidin-2-one obtained by the method of the present invention can be taken out and collected in a usual manner.

The 3,4-trans-4-ethyl-1-(substituted phenyl)-3-(substituted phenyl)pyrrolidin-2-one obtained by the method of the present invention can exert an excellent herbicidal activity. On the other hand, the cis isomer scarcely exhibits the herbicidal activity.

The compound of the formula (III) (hereinafter referred to as "the compound of the present invention") is a novel compound, and among the compounds of the formula (I), the compound of the present invention has particularly excellent characteristics as a herbicidal composition for paddy fields.

Compounds disclosed in U.S. Pat. Nos. 4,110,105, 4,210,589 and 4,874,422 have a pharmaceutically injurious action on rice plants, when used in paddy fields, and therefore they cannot be used therein.

In U.S. Pat. No. 4,960,457, compounds represented by the formula (II)

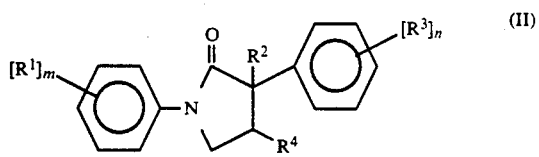

(wherein m is 1, 2, 3, 4 or 5; n is 0, 1, 2, 3, 4 or 5; $R^1$ is a halogen atom, trifluoromethyl group, cyano group, alkyl group having 1 to 4 carbon atoms or alkoxy group having 1 to 4 carbon atoms, and when m is more than 1, the groups of $R^1$ may be identical or different; $R^2$ is a hydrogen atom or halogen atom; $R^3$ is a halogen atom, trifluoromethyl group, cyano group, alkyl group having 1 to 4 carbon atoms or alkoxy group having 1 to 4 carbon atoms, and when n is more than 1, the groups of R3 may be identical or different; and R4 is an alkyl group having 1 to 4 carbon atoms or alkyl group having 1 to 4 carbon atoms which is substituted by a halogen) are claimed, and it is described in the patent that they have the herbicidal activity.

That is, the superior notion of U.S. Pat. No. 4,960,457 covers the compounds of the present invention. This U.S. patent claims the compounds in an extremely broad range, but the compounds in examples are limited. In the U.S. patent, it is described that the preferable examples of $R^1$ include a halogen atom, trifluoromethyl group and cyano group. However, in the examples of the U.S. patent, a trifluoromethyl group, cyano group, chlorine atom and fluorine atom are only described as the groups of $R^1$, and there is no example in which an alkyl group is used as the group of $R^1$.

The compounds described in U.S. Pat. No. 4,960,457 and E.P. Publication No. 387,869 are less effective to weeds in a growing period, when used in paddy fields. Therefore, the opportunity of using these compounds is limited to the period of the pre-emergence of the weeds.

The compound of the present invention is characterized in that a 3-isopropylphenyl group, a specific phenyl group and an ethyl group are introduced into the 1-position, the 3-position and the 4-position of the pyrrolidine ring, respectively. The significance that these particular groups are arranged, particularly the significance that the 3-isopropylphenyl group is introduced into the 1-position of the pyrrolidine ring is great. As a result of this conversion, the activity of the compound as the herbicidal composition for paddy fields can be heightened, and the compound can exhibit a high herbicidal activity in the period of from the pre-emergence of weeds to the growing period of the emerged weeds. In consequence, the compound of the present invention is applicable in a longer term.

The herbicidal composition for paddy fields containing the compound of the present invention as a herbicidally active ingredient has an excellent herbicidal effect to harmful weeds in most paddy fields, for example, gramineous weeds such as barnyard grass (*Echinohloa*) and the like, cyperaceous weeds such as *Cyperus microiria*, bulrush (*Sirpus juncoides*) and the like, and broadleaf weeds such as *Sagittaria pygmaea* and the like. On the other hand, the herbicidal composition has no injurious action on rice (*Oryza sativa*) which is an useful crop. Furthermore, the herbicidal composition can be effectively used in all applications such as submerged soil application, soil application and soil incorporation in the long term of from the pre-emergence of weeds to the growing period of the developed weeds.

The compound of the present invention is usually mixed with an inert liquid carrier or solid carrier, formulated in the form of powder, granules, wettable powder, emulsion, flowable formulation or the like, and then used. If required in the formulation, auxiliary agents can be added.

The carrier may be in the state of a solid or a liquid, and no particular restriction is put on the carrier, so long as it can be usually used in agents for agriculture and horticulture. Examples of the solid carrier include a mineral powder such as clay, talc, bentonite, calcium carbonate, diatomaceous earth and white carbon, vegetable powders such as a soybean powder and starch, and high polymer compounds such as petroleum resin, polyvinyl alcohol and polyalkylene glycols, urea and waxes. Furthermore, examples of the liquid carrier include various organic solvents such as xylene, methylnaphthalene and alkylbenzenes, various oils such as vegetable oils, and water.

Examples of the auxiliary agents include surfactants used in agents for agriculture and horticulture, binders (e.g., lignin sulfonic acid, alginic acid, polyvinyl alcohol, gum arabi and CMC sodium) and stabilizers (e.g., a light stabilizer can also be used, when a phenolic compound, thiol compound or higher fatty acid ester is utilized for the prevention of oxidation, or when a phosphate is utilized as a pH regulator), and they can be used singly or in combination. In certain cases, an industrial germicide or an antibacterial fungicide can be added for the control of bacteria and fungi.

Examples of the surfactant include non-ionic, anionic, cationic and amphoteric surfactants, which can be suitably used singly or in combination. A preferable example of the non-ionic surfactant can be obtained by adding ethylene oxide (e.g., X-77 or Neugen EA80) or propylene oxide to an alkylphenol, higher alcohol, alkylnaphthol, higher fatty acid, fatty acid ester or the like. A prferable example of the anionic surfactant is an alkylsulfonate salt (e.g., Neopelex), alkyl sulfate ester salt, phosphate ester salt or the like of an alkylphenol, alkylnaphthol, higher alcohol, higher fatty acid, fatty acid ester or the like. A lignine sulfonate salt (e.g., Sun Ekisu) or the like is also one preferable example.

The content of the compound represented by the formula (I) in the herbicidal composition of the present invention depends upon the morphology of the formulation. In general, it is 0.01–20% by weight in a powder, 1–50% by weight in a wettable powder, 0.01–10% by weight in granules, 0.1–50% by weight in an emulsion, 0.1–50% by weight in a flowable formulation and 1–50% by weight in a dry flowable formulation. Preferably, it is 0.1–3% by weight in a powder, 10–40% by weight in a wettable powder, 0.1–5% by weight in granules, 1–30% by weight in an emulsion, 1–30% by weight in a flowable formulation and 10–40% by weight in a dry flowable formulation.

The content of the auxiliary agents is 0–80% by weight, and the content of the carrier is a value obtained by subtracting the content of the herbicidally active ingredient compound and the auxiliary agents from 100% by weight.

The herbicidal composition of the present invention represented by the formula (I), needless to say, can be mixed with one or more of other herbicidal compositions or agricultural chemicals such as a fungicide, an insecticide and a plant growth regulator, a fertilizer, a soil improving agent and the like, and the herbicidal composition can also be prepared in the state of a mixed formulation therewith In some cases, a synergistic effect can be expected from such a combination.

The preparation methods of the present invention and preparation methods of compounds according to the present invention will be described in reference to typical examples.

EXAMPLE 1

35.1 g (0.10 mole) of 3,4-cis-4-ethyl-3-(3-fluorophenyl)-1-(3-trifluoromethylphenyl)pyrrolidin-2-one were dissolved in 300 ml of methanol, and 20 ml of a 50% aqueous sodium hydroxide solution were then added thereto with cooling. Afterward, the resultant solution was allowed to stand at room temperature for 5 hours. The solution was neutralized with concentrated hydrochloric acid, and most of methanol was then distilled off under reduced pressure. The residue was poured into 500 ml of water, and extraction was then made twice with 200 ml of ethyl acetate. After washing with an aqueous saturated sodium chloride solution and drying over anhydrous sodium sulfate, the solvent was distilled off under reduced pressure to obtain 34.6 g of white crystals of 3,4-trans-4-ethyl-3-(3-fluorophenyl)-1-(3-trifluoromethylphenyl)pyrrolidin-2-one (Compound No. 5).

The purity of the trans isomer by HPLC was 96%.

EXAMPLE 2

A mixture of 17.6 g (0.05 mole) of 3,4-cis-4-ethyl-3-(4-fluorophenyl)-1-(3-trifluoromethylphenyl)pyrrolidin-2-one and 17.6 g (0.05 mole) of 3,4-trans-4-ethyl-3-(4-fluorophenyl)-1-(3-trifluoromethylphenyl)pyrrolidin-2-one was dissolved in 300 ml of anhydrous tetrahydrofuran, and 5.0 g of 60% sodium hydride were added thereto with stirring under a nitrogen gas stream at room temperature and the solution was then maintained for 30 minutes. Next, the mixture was poured into 1000 ml of a 1% aqueous hydrochloric acid solution, and extraction was made twice with 200 ml of ethyl acetate, followed by washing with 300 ml of an aqueous saturated sodium chloride solution. The solvent was distilled off under reduced pressure to obtain 33.3 g of white crystals of 3,4-trans-4-ethyl-3-(4-fluorophenyl)-1-(3-trifluoromethylphenyl)pyrrolidin-2-one (Compound No. 3). The purity of the trans isomer by HPLC was 94%.

EXAMPLE 3

23.2 g (0.05 mole) of N-(2-butenyl)-N-(4-chloro-3-trifluoromethylphenyl)-2-bromo-2-(3-fluorophenyl)acetamide was dissolved in 200 ml of toluene, and 15 ml of tributyltin hydride and a trace amount of α,α-azobisisobutyronitrile were added thereto with stirring at 80°–90° C., followed by heating and stirring for 1 hour. After the solution was cooled to room temperature, 1.0 ml of 1,8-diazabicyclo(5.4.0)undec-7-ene (DBU) was added, and the solution was maintained for 1 hour. Next, the solution was washed with 100 ml of 10% hydrochloric acid, and toluene was then distilled off. The toluene-free solution was dissolved in 300 ml of acetonitrile and then washed with n-hexane sufficiently, and acetonitrile was distilled off to obtain 17.0 g of white crystals of 3,4-trans-4-ethyl-3-(3-fluorophenyl)-1-(4-chloro-3-trifluoromethylphenyl)pyrrolidin-2-one (Compound No. 33). The purity of the trans isomer by HPLC was 95%.

EXAMPLE 4

22.3 g (0.05 mole) of N-(2-butenyl)-N-(3-trifluoromethylphenyl)-2-bromo-2-(3-chlorophenyl)acetamide was dissolved in 200 ml of toluene, and 3.0 g of cuprous bromide and 3.0 ml of di-n-butylamine were then added thereto. The solution was maintained with stirring at 90°–100° C. for 30 minutes The resultant reaction mixture was poured into 20% hydrochloric acid and then extracted with toluene. The extract was dried over anhydrous magnesium sulfate, and the solvent was then distilled off. Silica gel chromatography was done to obtain 19.0 g of a steric isomer mixture of 4-(1-bromoethyl)-3-(3-chlorophenyl)-1-(3-trifluoromethylphenyl)-pyrrolidin-2-one. Next, the total amount of the mixture was dissolved in 300 ml of acetic acid saturated with hydrochloric acid, and 100 g of a zinc powder was then added thereto, followed by stirring at 90°–110° C. for 5 hours. Insolubles were removed by filtration, and an aqueous saturated sodium chloride solution was then poured. After extraction with toluene, the extract was then washed with an aqueous saturated sodium chloride solution sufficiently. 10.0 ml of 1,8-diazabicyclo(5.4.0)-undec-7-ene (DBU) were added, and the solution was then allowed to stand at room temperature for 1 hour. After washing with an aqueous dilute hydrochloric acid solution, toluene was distilled off, thereby obtaining 10.9 g of white crystals of 3,4-trans-4-ethyl-3-(3-chlorophenyl)-1-(3-trifluoromethylphenyl)pyrrolidin-2-one (Compound No. 11). The purity of the trans isomer by HPLC was 96%.

EXAMPLE 5

1.0 g of 4-ethyl-3-(3-fluorophenyl)-1-(4-chloro-3-isopropylphenyl)-pyrrolidin-2-one, 2.0 ml of formic acid and 0.7 g of 5% palladium carbon were added to 10 ml of dimethylformadmide, followed by stirring at a reflux temperature for 6 hours After palladium carbon was removed by filtration, extraction was carried out with toluene. After drying over anhydrous magnesium sulfate, the solution was concentrated by means of an evaporator to quantitatively obtain 3,4-trans-4-ethyl-3-(3-fluorophenyl)-1-(3-isopropylphenyl)pyrrolidin-2-one (Compound No. 58).

EXAMPLE 6

1.5 g of N-(2-butenyl)-N-(3-isopropylphenyl)-2-chloro-2-(3-chlorophenyl)acetamide were added to 15 ml of toluene, and 1.2 g of tributyltin hydride and a trace amount of α,α-azobisisobutyronitrile (AIBN) were added with stirring at a reflux temperature. After the stirring was continued for 10 minutes, the temperature of the solution was returned to room temperature, and 0.3 ml of DBU was added, followed by stirring additionally for 5 minutes. The reaction solution was concentrated by means of an evaporator and silica gel chromatography was then done to obtain 0.9 g of 3,4-trans-4-ethyl-3-(3-chlorophenyl)-1-(3-isopropylphenyl)-pyrrolidin-2-one (Compound No. 61).

COMPARATIVE EXAMPLE 1

23.2 g (0.05 mole) of N-(2-butenyl)-N-(4-chloro-3-trifluoromethylphenyl)-2-bromo-2-(3-fluorophenyl)acetamide were dissolved in 200 ml of toluene, and 15 ml of tributyltin hydride and a trace amount of α,α-azobisisobutyronitrile were added thereto with stirring at 80°–90° C., followed by heating and stirring for 1 hour Next, toluene was distilled off. The toluene-free solution was dissolved in 300 ml of acetonitrile and then washed with n-hexane sufficiently, and acetonitrile was then distilled off to obtain 17.0 g of an isomer mixture of 4-ethyl-3-(3-fluorophenyl)-1-(4-chloro-3-trifluoromethylphenyl)pyrrolidin-2-one. Silica gel chromatography was then done to obtain 9.2 g of 3,4-trans-4-ethyl-3-(3-fluorophenyl)-1-(4-chloro-3-trifluoromethylphenyl)-pyrrolidin-2-one and 3.5 g of 3,4-cis-4-ethyl-3-(3-fluorophenyl)-1-(4-chloro-3-trifluoromethylphenyl)pyrrolidin-2-one.

COMPARATIVE EXAMPLE 2

Reaction and treatment were carried out by the same procedure as in Example 2 except that DBU was not added, thereby obtaining 10.6 g of an isomer mixture of 4-ethyl-3-(3-chlorophenyl)-1-(3-trifluoromethylphenyl)pyrrolidin-2-one. Silica gel chromatography was then done to obtain 6.8 g of 3,4-trans-4-ethyl-3-(3-chlorophenyl)-1-(3-trifluoromethylphenyl)pyrrolidin-2-one and 3.3 g of 3,4-cis-4-ethyl-3-(3-chlorophenyl)-1-(3-trifluoromethylphenyl)pyrrolidin-2-one.

REFERENCE EXAMPLES

Synthesis examples of N-(2-butenyl)-N-(substituted phenyl)-2-halo-2-(substituted phenyl)acetamides, N-(2-butenyl)anilines and α-halo-phenylacetic acid halides will be described as reference examples

REFERENCE EXAMPLE 1

Synthesis of N-(2-butenyl)-N-(3-trifluoromethylphenyl)-2-bromo-2-(3-chlorophenyl)acetamides:

3.0 g of 2-bromo-2-(3-chlorophenyl)acetyl chloride were gradually added dropwise to 2.2 g of N-(2-butenyl)-N-(3-trifluoromethylphenyl)amine in 40 ml of toluene with stirring in the vicinity of room temperature. After stirring additionally for 20 minutes, precipitated insolubles were removed by filtration, and the solution was then diluted with toluene. The toluene solution was sufficiently washed with an aqueous saturated sodium bicarbonate solution and an aqueous saturated sodium chloride solution. After drying over anhydrous sodium sulfate, the solvent was distilled off to quantitatively obtain the desired oily product.

REFERENCE EXAMPLE 2

Synthesis of N-(2-butenyl)-N-(3-trifluoromethylphenyl)amine:

1.4 g of anhydrous potassium carbonate and 1.0 g of 1-chloro-2-butene were added to 1.6 g of 3-aminobenzotrifluoride in 30 ml of dimethylformamide, followed by stirring at 70°–90° C. for 2 hours. Potassium carbonate was then removed by filtration, and 100 ml of an aqueous saturated sodium chloride solution were added and extraction was then carried out with toluene. After drying over anhydrous sodium sulfate, the solvent was distilled off, and silica gel chromatography was then done to obtain 1.4 g of the desired compound.

REFERENCE EXAMPLE 3

Synthesis of 2-bromo-2-(3-chlorophenyl)acetyl chloride:

14 g of thionyl chloride were added to 17.1 g of 3-chlorophenylacetic acid, and 18 g of bromine was added dropwise thereto with stirring, while the solution was heated under reflux. After the addition, the heating under reflux was continued for 30 hours. After cooling, the solution was concentrated by means of an evaporator to quantitatively obtain the desired compound.

REFERENCE EXAMPLE 4

Synthesis of 3,4-trans-4-ethyl-3-(3-fluorophenyl)-1-(4-chloro-3-isopropylphenyl)pyrrolidin-2-one (the intermediate of Compound No. 58)

2.0 g of N-(2-butenyl)-N-(4-chloro-3-isopropylphenyl)-2-chloro-2-(3-fluorophenyl)acetamide were added to 15 ml of toluene, and 1.8 g of tributyltin hydride and a trace amount of α,α-azobisisobutyronitrile (AIBN) were added with stirring at a reflux temperature. After the stirring was continued for 10 minutes, the temperature of the solution was returned to room temperature, and 0.3 ml of DBU was added thereto, followed by stirring additionally for 5 minutes. The reaction solution was concentrated by means of an evaporator and silica gel chromatography was then done to obtain 1.4 g of the desired compound.

IR ν neat (cm$^{-1}$) 1702.

NMR (CDCl$_3$) δ ppm: 0.97 (3H, t, J=7.2 Hz), 1.21–1.27 (6H, m), 1.50–1.60 (1H, m), 1.70–1.80 (1H, m), 2.40–2.50 (1H, m), 3.35–3.45 (1H, m), 3.48 (1H, d, J=10.4 Hz), 3.54 (1H, t, J=8.8 Hz), 3.99 (1H, t, J=8.8 Hz), 6.96–7.06 (3H, m), 7.26–7.37 (3H, m), 7.76 (1H, s).

The same procedure as in Reference Example 4 was effected to synthesize the following pyrrolidine derivatives. The derivatives thus obtained have the following physical properties:

3,4-trans-4-ethyl-3-(3,5-difluorophenyl)-1-(4-chloro-3-isopropylphenyl)pyrrolidin-2-one (the intermediate of Compound No. 59)

IR ν neat (cm$^{-1}$): 1702,
$n_D$ 22.2° C.: 1.5398.

3,4-trans-4-ethyl-3-(3,4-difluorophenyl)-1-(4-chloro-3-isopropylphenyl)pyrrolidin-2-one (the intermediate of Compound No. 60)

IR ν neat (cm$^{-1}$): 1701,
$n_D$ 23.1° C.: 1.5670.

REFERENCE EXAMPLE 5

Synthesis of N-(2-butenyl)-N-(4-chloro-3-isopropylphenyl)-2-chloro-2-(3-fluorophenyl)acetamide 2.6 g of 2-chloro-2-(3-fluorophenyl)acetyl chloride were gradually added dropwise to 2.2 g of N-(2-butenyl)-N-(4-chloro-3-isopropylphenyl)amine and 2.0 g of anhydrous potassium carbonate in 40 ml of N,N-dimethylformamide with stirring at 20°-30° C. After the stirring was additionally continued for 20 minutes, potassium carbonate was removed by filtration, and extraction was then carried out with toluene. After drying over anhydrous sodium sulfate, the reaction solution was concentrated by means of an evaporator to quantitatively obtain the desired oily product.

IR ν neat (cm$^{-1}$): 1679.
$n_D$ 32.1° C.: 1.5502.

The same procedure as in Reference Example 5 was effected to synthesize other amide derivatives. The derivatives thus obtained have the following physical properties:

N-(2-butenyl)-N-(4-chloro-3-isopropylphenyl)-2-chloro-2-(3,5-difluorophenyl)acetamide:

IR ν neat (cm$^{-1}$): 1680.
$n_D$ 24.6° C.: 1.5175,

N-(2-butenyl)-N-(4-chloro-3-isopropylphenyl)-2-bromo-2-(3,4-difluorophenyl)acetamide IR ν neat (cm$^{-1}$): 1677.
$n_D$ 24.2° C.: 1.5497.

N-(2-butenyl)-N-(3-isopropylphenyl)-2-chloro-2-(3-chlorophenyl)acetamide

IR ν neat (cm$^{-1}$): 1676.
$n_D$ 21.4° C.: 1.5617.

REFERENCE EXAMPLE 6

Synthesis of N-(2-butenyl)-N-(4-chloro-3-isopropylphenyl)amine:

2.8 g of anhydrous potassium carbonate and 2.0 g of -chloro-2-butene were added to 3.2 g of 4-chloro-3-isopropylaniline in 15 ml of N,N-dimethylformamide, followed by stirring at 70°-90° C. for 1 hour. After potassium carbonate was removed by filtration, 100 ml of water were added, and extraction was then carried out with toluene. After drying over anhydrous sodium sulfate, the reaction solution was concentrated by means of an evaporator, and silica gel chromatography was then done to obtain 1.5 g of the desired compound.

IR ν neat (cm$^{-1}$): 3418.
$n_D$ 23.0° C.: 1 5145.

Furthermore, N-(2-butenyl)-N-(3-isopropylphenyl)amine was synthesized in the same manner.

IR ν neat (cm-1): 3413.
$n_D$ 21.4° C.: 1.5303.

REFERENCE EXAMPLE 7

Synthesis of 3,4-cis-4-ethyl-3-(3-chlorophenyl)-1-(3-isopropylphenyl)pyrrolidin-2-one (Comparative Compound E)

2.0 g of N-(2-butenyl)-N-(3-isopropylphenyl)-2-chloro-2-(3-chlorophenyl)acetamide was added to 15 ml of toluene, and 1.7 g of tributyltin hydride and a trace amount of α,α-azobisisobutyronitrile (AIBN) were added to the solution with stirring at a reflux temperature. After the stirring was continued for 10 minutes, the temperature of the solution was returned to room temperature, and the reaction solution was concentrated by means of an evaporator and column chromatography was then done to obtain 0.9 g of the first eluted compound, 3,4-trans--ethyl-3-(3-chlorophenyl)-1-(3-isopropylphenyl)pyrrolidin-2-one (Compound No. 61) and 0.3 g of the last eluted compound, 3,4-cis-4-ethyl-3-(3-chlorophenyl)-1-(3-isopropylphenyl)pyrrolidin-2-one (Compound No. E).

IR ν nujol (cm$^{-1}$): 1702.

NMR (CDCl$_3$) δ ppm: 0.91 (3H, t, J=7.6 Hz), 1.24 (6H, d, J=6.6 Hz), 1.21-1.75 (2H, m), 2.63-2.74 (1H, m), 2.80-2.95 (1H, m), 3.69 (1H, dd, J=7.4 Hz, 9.3 Hz), 4.00 (1H, d, J=8.9 Hz), 4.03 (1H, dd, J=7.3 Hz, 9.3 Hz), 7.03 (1H, d, J=8.0 Hz), 7.13 (1H, d, J=7.3 Hz), 7.20-7.66 (6H, m).

The steric conformation at the 3- and 4-positions of a pyrrolidinone ring is decided by the coupling constants of the proton (which is represented by 3-H) at the 3-position of the pyrrolidinone ring and the proton (which is represented by 4-H) at the 4-position of the pyrrolidinone ring. That is, in the case of 4-ethyl-3-(3-chlorophenyl)-1-(3-isopropylphenyl)-2-pyrrolidinon-2-one, the 3,4-trans isomer is decided by $J_{3H-4H}$=10.3 Hz, and the 3,4-cis isomer is decided by $J_{3H-4H}$=8.9 Hz.

Table 1 shows examples of the compounds (Compound Nos. 1-57) represented by the formula (I) regarding the preparation method of the present invention and the compounds (Compound Nos. 58-62) represented by the formula (III) of the present invention.

TABLE 1

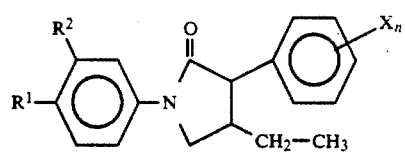

(I)

| Compound No. | Substituents in formula (I) | | | Physical Properties |
|---|---|---|---|---|
| | R$^1$ | R$^2$ | X$_n$ | |
| 1 | H | CF$_3$ | H | 3,4-trans NMR(100MHz, CDCl$_3$)δppm: 1.00(3H, t, J=7Hz), 1.50-1.90(2H, m), 2.30-2.80(1H, m), 3.54(1H, d, J=10Hz), 3.61(1H, t, J=8Hz), 4.06(1H, dd, J=8Hz, 9Hz), 7.20-7.75(7H, m), 7.95-8.15(2H, m) |

TABLE 1-continued

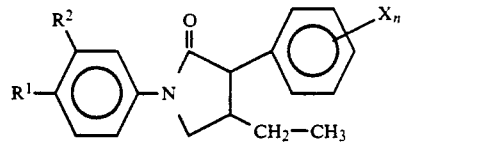

| Compound No. | Substituents in formula (I) | | | | Physical Properties |
|---|---|---|---|---|---|
| | R¹ | R² | $X_n$ | | |
| 2 | H | $CF_3$ | H | 3,4-cis | IR ν neat cm⁻¹: 1700<br>NMR(100MHz, CDCl₃)δppm: 0.96(3H, t, J=7Hz),<br>1.23-1.74(2H, m), 2.50-2.85(1H, m),<br>3.70(1H, dd, J=7Hz, 8Hz), 3.98(1H, d, J=8Hz),<br>4.04(1H, t, J=7Hz), 7.10-7.60(7H, m),<br>8.00-8.15(2H, m) |
| 3 | H | $CF_3$ | 4-F | 3,4-trans | IR ν neat cm⁻¹: 1700<br>NMR(100MHz, CDCl₃)δppm: 1.00(3H, t, J=7Hz),<br>1.45-190(2H, m), 2.20-2.65(1H, m),<br>3.49(1H, d, J=10Hz), 3.58(1H, t, J=8Hz),<br>4.03(1H, dd, J=8Hz, 9Hz), 6.96-7.37(4H, m),<br>7.40-7.60(2H, m), 7.80-8.05(2H, m) |
| 4 | H | $CF_3$ | 4-F | 3,4-cis | IR ν nujol cm⁻¹: 1700, m.p. 82-84.0° C.<br>NMR(100MHz, CDCl₃)δppm: 0.95(3H, t, J=7Hz),<br>1.25-1.75(2H, m), 2.50-2.80(1H, m),<br>3.67(1H, dd, J=7Hz, 8Hz), 4.02(1H, d, J=9Hz),<br>4.05(1H, t, J=7Hz), 6.96-7.28(4H, m),<br>7.36-7.64(2H, m), 7.86-8.05(2H, m) |
| 5 | H | $CF_3$ | 3-F | 3,4-trans | IR ν neat cm⁻¹: 1700<br>NMR(270MHz, CDCl₃)δppm: 0.99(3H, t, J=7.6Hz),<br>1.49-1.60(1H, m), 1.70-1.81(1H, m),<br>2.41-2.56(1H, m), 3.51(1H, d, J=10.5Hz),<br>3.60(1H, t, J=9.5Hz), 4.04(1H, dd, J=7.8Hz,<br>9.5Hz), 6.97-7.07(3H, m), 7.31-7.53(3H, m),<br>7.93-7.96(2H, m) |
| 6 | H | $CF_3$ | 3-F | 3,4-cis | IR ν nujol cm⁻¹: 1700, m.p. 98.5-100.0° C<br>NMR(270MHz, CDCl₃)δppm: 0.92(3H, t, J=7.8Hz),<br>1.22-1.73(2H, m), 2.63-2.74(1H, m),<br>3.69(1H, dd, J=7.4Hz, 9.3Hz), 4.00(1H, d,<br>J=8.9Hz), 4.03(1H, dd, J=7.3Hz, 9.3Hz),<br>6.87-7.10(3H, m), 7.25-7.57(3H, m),<br>7.93-8.04(2H, m) |
| 7 | H | $CF_3$ | 4-$CF_3$ | 3,4-trans | IR ν neat cm⁻¹: 1700<br>NMR(270MHz, CDCl₃)δppm: 0.99(3H, t, J=7.5Hz),<br>1.50-1.66(1H, m), 1.68-1.85(1H, m),<br>2.45-2.58(1H, m), 3.58(1H, d, J=10.3Hz),<br>3.63(1H, t, J=9.5Hz), 4.06(1H, dd, J=7.3Hz,<br>9.5Hz), 7.40(2H, d, J=7.8Hz), 7.44-7.56<br>(2H, m), 7.65(2H, d, J=7.8Hz), 7.87-7.96<br>(2H, m) |
| 8 | H | $CF_3$ | 4-$CF_3$ | 3,4-cis | IR ν nujol cm⁻¹: 1700, m.p. 94.5-96.4° C.<br>NMR(270MHz, CDCl₃)δppm: 0.92(3H, t, J=7.3Hz),<br>1.18-1.75(2H, m), 2.63-2.78(1H, m), 3.70<br>(1H, dd, J=6.9Hz, 10.0Hz), 4.06(1H, dd,<br>J=8.1Hz, 10.0Hz), 4.08(1H, d, J=8.9Hz),<br>7.25-7.29(2H, m), 7.42-7.65(4H, m),<br>7.94-8.04(2H, m) |
| 9 | H | $CF_3$ | 3-$CF_3$ | 3,4-trans | IR ν neat cm⁻¹: 1700<br>NMR(270MHz, CDCl₃)δppm: 0.99(3H, t, J=7.3Hz),<br>1.48-1.62(1H, m), 1.70-1.82(1H, m),<br>2.43-2.59(1H, m), 3.58(1H, d, J=10.5Hz),<br>3.63(1H, t, J=9.5Hz), 4.06(1H, dd, J=7.8Hz,<br>9.5Hz), 7.36-7.60(6H, m), 7.92-7.97(2H, m) |
| 10 | H | $CF_3$ | 3-$CF_3$ | 3,4-cis | IR ν nujol cm⁻¹: 1700, m.p. 87.0-88.5° C.<br>NMR(270MHz, CDCl₃)δppm: 0.89(3H, t, J=7.3Hz),<br>1.18-1.74(2H, m), 2.63-2.77(1H, m),<br>3.71(1H, dd, J=6.9Hz, 9.5Hz), 4.05(1H, dd,<br>J=8.0Hz, 10.0Hz), 4.09(1H, d, J=8.4Hz),<br>7.30-7.65(6H, m), 7.93-8.03(2H, m) |
| 11 | H | $CF_3$ | 3-Cl | 3,4-trans | IR ν neat cm⁻¹: 1705<br>NMR(270MHz, CDCl₃)δppm: 0.99(3H, t, J=7.6Hz),<br>1.48-1.65(1H, m), 1.70-1.85(1H, m),<br>2.40-2.55(1H, m), 3.49(1H, d, J=10.3Hz),<br>3.60(1H, t, J=9.5Hz), 4.03(1H, dd, J=7.6Hz,<br>9.5Hz), 7.10-7.19(1H, m), 7.25-7.50(5H, m),<br>7.92-7.97(2H, m) |
| 12 | H | $CF_3$ | 3-Cl | 3,4-trans | IR ν nujol cm⁻¹: 1705, m.p. 105.9-106.8° C<br>NMR(270MHz, CDCl₃)δppm: 0.92(3H, t, J=7.3Hz),<br>1.18-1.74(2H, m), 2.60-2.74(1H, m),<br>3.69(1H, dd, J=7.2Hz, 9.5Hz), 3.98(1H, d,<br>J=8.9Hz), 4.03(1H, dd, J=7.6Hz, 9.5Hz), |

TABLE 1-continued (I)

Structure: R¹ and R² substituted phenyl connected to N of pyrrolidinone ring (with C=O), 3-position bears phenyl with $X_n$ substituents, 4-position bears $CH_2-CH_3$.

| Compound No. | R¹ | R² | Xₙ | | Physical Properties |
|---|---|---|---|---|---|
| | | | | | 7.02–7.07(1H, m), 7.16(1H, m), 7.26–7.35 (2H, m), 7.43–7.56(2H, m), 7.93–8.03(2H, m) IR ν neat cm⁻¹: 1700 |
| 13 | H | CF₃ | 3,5-F₂ | 3,4-trans | NMR(270MHz, CDCl₃)δppm: 0.97(3H, t, J=7.6Hz), 1.50–1.67(1H, m), 1.70–1.85(1H, m), 2.40–2.55(1H, m), 3.50(1H, d, J=10.5Hz), 3.61(1H, t, J=9.5Hz), 4.04(1H, dd, J=7.8Hz, 9.5Hz), 6.73–6.86(3H, m), 7.41–7.54(2H, m), 7.89–7.96(2H, m) IR ν KBr cm⁻¹: 1690, m.p. 88.2–89.7° C. |
| 14 | H | CF₃ | 3,5-F₂ | 3,4-cis | IR ν KBr cm⁻¹: 1690, m.p. 90.0–95.0° C |
| 15 | H | CF₃ | 3,4-F₂ | 3,4-trans | NMR(270MHz, CDCl₃)δppm: 0.96(3H, t, 7.3Hz), 1.46–1.66(1H, m), 1.70–1.85(1H, m), 2.37–2.49(1H, m), 3.47(1H, d, J=10.8Hz), 3.60(1H, t, J=9.5Hz), 4.03(1H, dd, J=7.8Hz, 9.5Hz), 6.97–7.23(3H, m), 7.41–7.54(2H, m), 7.91–7.95(2H, m) IR ν nujol cm⁻¹: 1700, m.p. 76.5–80.5° C. |
| 16 | H | CF₃ | 3,4-F₂ | 3,4-cis | NMR(270MHz, CDCl₃)δppm: 0.95(3H, t, J=7.3Hz), 1.22–1.72(2H, m), 2.60–2.73(1H, m), 3.67(1H, t, J=9.4Hz), 3.98(1H, d, J=8.4Hz), 4.03(1H, dd, J=9.4Hz, 7.4Hz), 6.90–7.20(3H, m), 7.43–7.57(2H, m), 7.92–8.02(2H, m) IR ν neat cm⁻¹: 1700 |
| 17 | H | CF₃ | 3-CH₃ | 3,4-trans | NMR(270MHz, CDCl₃)δppm: 0.95(3H, t, J=7.9Hz), 1.48–1.68(1H, m), 1.70–1.85(1H, m), 2.37(3H, s), 2.41–2.56(1H, m), 3.46(1H, d, J=10.4Hz), 3.58(1H, t, J=8.9Hz), 4.04(1H, dd, J=7.9Hz), 7.04–7.13(3H, m), 7.21–7.32 (1H, m), 7.42–7.53(2H, m), 7.89–7.99(2H, m) IR ν neat cm⁻¹: 1700 |
| 18 | H | CF₃ | 3-CH₃ | 3,4-cis | NMR(270MHz, CDCl₃)δppm: 0.95(3H, t, J=7.3Hz), 1.20–1.70(2H, m), 2.32(3H, s), 2.58–2.72 (1H, m), 3.72(1H, t, J=8.4Hz), 3.94(1H, d, J=8.4Hz), 4.00(1H, dd, J=7.9Hz, 8.4Hz), 6.87–6.93(1H, m), 7.05–7.11(1H, m), 7.15–7.25(2H, m), 7.42–7.58(2H, m), 7.95 (1H, broad s), 8.03–8.06(1H, m) IR ν neat cm⁻¹: 1700 |
| 19 | H | CF₃ | 2,4-F₂ | 3,4-trans | NMR(270MHz, CDCl₃)δppm: 0.98(3H, t, J=7.6Hz), 1.51–1.80(2H, m), 2.41–2.53(1H, m), 3.60(1H, t, J=9.2Hz), 3.71(1H, d, J=10.8Hz), 4.03(1H, dd, J=7.9Hz, 9.2Hz), 6.80–6.92 (2H, m), 7.15–7.25(1H, m), 7.38–7.55 (2H, m), 7.80–8.00(2H, m) IR ν neat cm⁻¹: 1690 |
| 20 | H | CF₃ | 2,4-F₂ | 3,4-cis | NMR(270MHz, CDCl₃)δppm: 0.91(3H, t, J=7.3Hz), 1.20–1.75(2H, m), 2.63–2.75(1H, m), 3.68(1H, t, J=9.4Hz), 4.01(1H, d, J=8.4Hz), 4.03(1H, dd, J=9.4Hz, 7.4Hz), 6.78–6.90 (2H, m), 7.14–7.24(1H, m), 7.38–7.56 (2H, m), 7.80–8.00(2H, m) IR ν neat cm⁻¹: 1700 |
| 21 | H | CF₃ | 3,5-Cl₂ | 3,4-trans | NMR(270MHz, CDCl₃)δppm: 1.00(3H, t, J=7.4Hz), 1.50–1.82(2H, m), 2.43–2.51(1H, m), 3.46 (1H, d, J=10.9Hz), 3.60(1H, t, J=8.9Hz), 4.04(1H, t, J=8.9Hz), 7.16(2H, d, J=1.5Hz), 7.29–7.35(1H, m), 7.42–7.54(2H, m), 7.89–7.96(2H, m) IR ν neat cm⁻¹: 1700 |
| 22 | H | CF₃ | 3,5-Cl₂ | 3,4-cis | NMR(270MHz, CDCl₃)δppm: 0.92(3H, t, J=7.4Hz), 1.20–1.65(2H, m), 2.60–2.70(1H, m), 3.70 (1H, dd, J=6.9Hz, 9.9Hz), 3.97(1H, d, J=8.4Hz), 4.04(1H, dd, 7.4Hz, 9.9Hz), 7.08(2H, d, J=1.5Hz), 7.30–7.35(1H, m), 7.44–7.57(2H, m), 7.91–8.02(2H, m) IR ν neat cm⁻¹: 1700 |
| 23 | H | CF₃ | 2,3-Cl₂ | 3,4-trans | NMR(270MHz, CDCl₃)δppm: 0.98(3H, t, J=7.4Hz), 1.45–1.80(2H, m), 2.52–2.63(1H, m), 3.64 (1H, t, J=8.9Hz), 4.03(1H, d, J=9.5Hz), 4.08(1H, t, J=8.9Hz), 7.14(1H, dd, J=1.5Hz, |

TABLE 1-continued

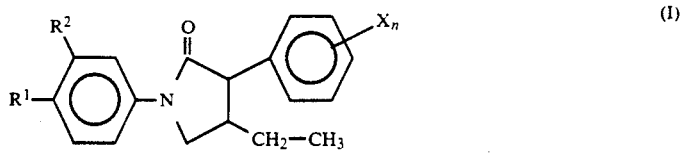

(I)

| Compound No. | Substituents in formula (I) | | | Physical Properties |
|---|---|---|---|---|
| | R¹ | R² | $X_n$ | |
| | | | | 7.9Hz), 7.22(1H, dd, J=1.5Hz, 7.9Hz), 7.42-7.46(2H, m), 7.51(1H, t, J=7.9Hz), 7.91-7.98(2H, m) IR ν neat cm⁻¹: 1700 |
| 24 | H | CF₃ | 2,3-Cl₂  3,4-cis | NMR(270MHz, CDCl₃)δppm: 0.92(3H, t, J=7.4Hz), 1.25-1.70(2H, m), 2.75-2.90(1H, m), 3.68 (1H, dd, J=3.9Hz, 9.9Hz), 4.10(1H, dd, J=6.9Hz, 9.9Hz), 4.63(1H, d, J=8.9Hz), 7.21-7.26 (2H, m), 7.39-7.57(3H, m), 7.95-8.00(2H, m) IR ν neat cm⁻¹: 1700 |
| 25 | H | CF₃ | 3-Br  3,4-trans | NMR(270MHz, CDCl₃)δppm: 0.98(3H, t, 7.4Hz), 1.48-1.85(2H, m), 2.40-2.55(1H, m), 3.47 (1H, d, J=10.3Hz), 3.59(1H, t, J=8.9Hz), 4.03(1H, dd, J=8.2Hz, 8.9Hz), 7.12-7.53 6H, m), 7.92-7.97(2H, m) IR ν nujol cm⁻¹: 1700, m.p. 95.2-96.8° C. |
| 26 | H | CF₃ | 3-Br  3,4-cis | NMR(270MHz, CDCl₃)δppm: 0.92(3H, t, 7.3Hz), 1.20-1.73(2H, m), 2.60-2.74(1H, m), 3.70 (1H, t, J=9.2Hz), 3.99(1H, t, J=9.2Hz), 4.00(1H, d, J=8.5Hz), 7.05-7.55(6H, m), 7.93-8.03(2H, m) IR ν neat cm⁻¹: 1700 |
| 27 | H | CF₃ | 4-Cl  3,4-trans | NMR(270MHz, CDCl₃)δppm: 0.98(3H, t, J=7.3Hz), 1.48-1.82(2H, m), 2.38-2.52(1H, m), 3.48(1H, d, J=10.3Hz), 3.59(1H, t, J=8.9Hz), 4.02(1H, t, J=8.9Hz), 7.15-7.27(3H, m), 7.32-7.52(3H, m), 7.88-7.97(2H, m) IR ν neat cm⁻¹: 1700 |
| 28 | H | CF₃ | 4-Cl  3,4-cis | NMR(270MHz, CDCl₃)δppm: 0.93(3H, t, J=7.3Hz), 1.24-1.73(2H, m), 2.58-2.72(1H, m), 3.67(1H, dd, J=7.5Hz, 9.9Hz), 3.98(1H, d, J=8.9Hz), 4.02(1H, dd, J=7.5Hz, 9.5Hz), 7.07-7.58(6H, m), 7.92-8.03(2H, m) IR ν neat cm⁻¹: 1700 |
| 29 | H | CF₃ | 3-NO₂  3,4-trans | NMR(270MHz, CDCl₃)δppm: 0.97(3H, t, J=7.4Hz), 1.55-1.83(2H, m), 2.50-2.65(1H, m), 3.64(1H, d, J=9.2Hz), 3.66(1H, t, J=9.2Hz), 4.08(1H, dd, J=8.0Hz, 9.2Hz), 7.40-7.67(4H, m), 7.90-7.97(2H, m), 8.15-8.23(2H, m) IR ν neat cm⁻¹: 1700 |
| 30 | H | CF₃ | 3-NO₂  3,4-cis | NMR(270MHz, CDCl₃)δppm: 0.92(3H, t, J=7.4Hz), 1.23-1.73(2H, m), 2.60-2.72(1H, m), 3.69 (1H, t, J=7.7Hz), 3.95(1H, d, J=8.2Hz), 4.01(1H, t, J=7.7Hz), 7.38-7.66(4H, m), 7.89-7.98(2H, m), 8.13-8.24(2H, m) IR ν neat cm⁻¹: 1700 |
| 31 | F | CF₃ | 3-F  3,4-trans | NMR(270MHz, CDCl₃)δppm: 0.99(3H, t, J=7.4Hz), 1.49-1.65(1H, m), 1.70-1.83(1H, m), 2.43-2.54(1H,m), 3.50(1H, d, J=10.4Hz), 3.58(1H, t, J=9.4Hz), 4.00(1H, dd, J=7.8Hz, 9.4Hz), 6.95-7.08(3H, m), 7.16-7.39(2H, m), 7.86-7.97(2H,m) IR ν neat cm⁻¹: 1700, m.p. 116.6-117.8°C. |
| 32 | F | CF₃ | 3-F  3,4-cis | NMR(270MHz, CDCl₃)δppm: 0.92(3H, t, J=7.4Hz), 1.30-1.72(2H, m), 2.63-2.74(1H, m), 3.66 (1H, dd, J=7.4Hz, 9.4Hz), 3.96-4.05(2H, m), 6.84-7.03(3H, m), 7.21-7.35(2H, m), 7.88-7.91(1H, m), 7.99-8.04(1H, m) IR ν neat cm⁻¹: 1705 |
| 33 | Cl | CF₃ | 3-F  3,4-trans | NMR(270MHz, CDCl₃)δppm: 0.96(3H, t, J=7.5Hz), 1.48-1.65(1H, m), 1.70-1.85(1H, m), 2.40-2.55(1H, m), 3.50(1H, d, J=10.3Hz), 3.57(1H, t, J=9.1Hz), 4.01(1H, t, J=9.1Hz), 6.95-7.09(3H, m), 7.31-7.39(1H, m), 7.50 (1H, d, J=8.9Hz), 7.90(1H, dd, J=8.9Hz, 2.4Hz), 8.00(1H, d, J=2.4Hz) IR ν nujol cm⁻¹: 1700, m.p. 131.3-133.2° C. |
| 34 | Cl | CF₃ | 3-F  3,4-cis | NMR(270MHz, CDCl₃)δppm: 0.92(3H, t, J=7.3Hz), 1.24-1.74(2H, m), 2.60-2.74(1H, m), 3.66 (1H, dd, J=9.3Hz, 7.1Hz), 3.99(1H, d, J=8.4), 4.00(1H, dd, J=9.3Hz, 7.4Hz), 6.84-7.05 |

TABLE 1-continued

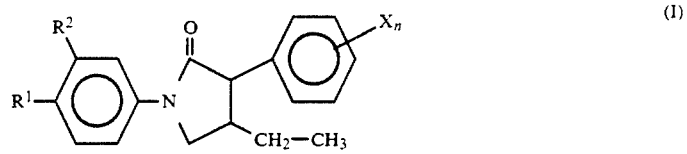

| Compound No. | R¹ | R² | Xₙ | | Physical Properties |
|---|---|---|---|---|---|
| | | | | | (3H, m), 7.23-7.35(1H, m), 7.52(1H, d, J=8.4Hz), 7.97-8.05(2H, m)<br>IR ν neat cm⁻¹: 1700 |
| 35 | H | CF₃ | 3-CN | 3,4-trans | NMR(270MHz, CDCl₃)δppm: 0.99(3H, t, J=7.3Hz), 1.51-1.84(2H, m), 2.41-2.57(1H, m), 3.56 (1H, d, J=10.3Hz), 3.64(1H, t, J=9.5Hz), 4.06(1H, dd. J=7.8Hz, 9.5Hz), 7.42-7.64 (6H, m), 7.85-7.95(2H, m)<br>IR ν nujol cm⁻¹: 2230, 1700, m.p. 113.0-115.5° C. |
| 36 | H | CF₃O | 3-F | 3,4-trans | NMR(400MHz, CDCl₃)δppm: 1.02(3H, t, J=7.3Hz), 1.50-1.66(1H, m), 1.71-1.81(1H, m), 2.41-2.52(1H, m), 3.50(1H, d, J=10.0Hz), 3.55(1H, t, J=8.8Hz), 4.03(1H, t, J=8.8Hz), 6.96-7.05(4H, m), 7.30-7.42(2H, m), 7.62(1H, m), 7.68(1H, m)<br>IR ν neat cm⁻¹: 1705 |
| 37 | H | HCF₂O | 3-F | 3,4-trans | NMR(400MHz, CDCl₃)δppm: 0.97(3H, t, J=7.3Hz), 1.52-1.64(1H, m), 1.72-1.81(1H, m), 2.42-2.49(1H, m), 3.49(1H, d, J=10.3Hz), 3.55(1H, t, J=8.8Hz), 4.00(1H, t, J=8.8Hz), 6.54(1H, t, J=74.0Hz), 6.91-7.05(4H, m), 7.32-7.38(2H, m), 7.49(1H, dd, J=1.5Hz, 81Hz), 7.61(1H,m)<br>IR ν neat cm⁻¹: 1702 |
| 38 | H | CF₂BrO | 3-F | 3,4-trans | NMR(400MHz, CDCl₃)δppm: 0.98(3H, t, J=7.3Hz), 1.53-1.64(1H, m), 1.73-1.80(1H, m), 2.44-2.51(1H, m), 3.50(1H, d, J=10.3Hz), 3.54(1H, t, J=9.5Hz), 4.01(1H, dd, J=8.0Hz, 9.5Hz), 6.96-7.07(4H, m), 7.32-7.43(2H, m), 7.64-7.69(2H, m)<br>IR ν neat cm⁻¹: 1707 |
| 39 | H | HCF₂CF₂O | 3-F | 3,4-trans | NMR(400MHz, CDCl₃)δppm: 0.98(3H, t, J=7.3Hz), 1.50-1.62(1H, m), 1.71-1.81(1H, m), 2.41-2.51(1H, m), 3.49(1H, d, J=10.3Hz), 3.55(1H, t, J=9.5Hz), 4.00(1H, dd, J=8.1Hz, 9.5Hz), 5.90(1H, dt, J=2.9Hz, 53.0Hz), 6.96-7.05(4H, m), 7.31-7.40(2H, m), 7.58-7.60(1H, m), 7.65(1H, d, J=2.2Hz)<br>IR ν neat cm⁻¹: 1703 |
| 40 | H | HCF₂CF₂O | 3-Cl | 3,4-trans | NMR(400MHz, CDCl₃)δppm: 0.98(3H, t, J=7.3Hz), 1.50-1.62(1H, m), 1.70-1.79(1H, m), 2.41-2.51(1H; m), 3.47(1H, d, J=11.0Hz), 3.55(1H, t, J=9.5Hz), 4.00(1H, dd, J=8.1Hz, 9.5Hz), 5.90(1H, dt, J=2.9Hz, 53.0Hz), 7.04(1H, d, J=7.3Hz), 7.15(1H, m), 7.25-7.40(4H, m), 7.59(1H, dd, J=1.4Hz, 8.1Hz), 7.65(1H, broad s)<br>IR ν neat cm⁻: 1702 |
| 41 | H | CH₃ | 3-Cl | 3,4-trans | NMR(400MHz, CDCl₃)δppm: 0.97(3H, t, J=7.3Hz), 1.51-1.59(1H, m), 1.71-1.78(1H, m), 2.37 (3H, s), 2.39-2.46(1H, m), 3.48(1H, d, J=10.3Hz), 3.57(1H, t, J=8.8Hz), 3.99 (1H, dd, J=8.1Hz, 9.5Hz), 6.96-7.06(4H, m), 7.24-7.34(2H, m), 7.42(1H, d, J=8.1Hz), 7.54(1H, s)<br>IR ν KBr cm⁻¹: 1700, m.p. 81.0-84.0° C. |
| 42 | H | CH₃ | 3-F | 3,4-cis | NMR(400MHz, CDCl₃)δppm: 0.88(3H, t, J=7.4Hz), 1.00-1.30(2H, m), 2.35(3H, s), 2.60-2.70 (1H, m), 3.70-3.73(1H, m), 3.94-4.02(2H, m), 6.90-7.07(4H, m), 7.22-7.40(2H, m), 7.50-7.67(2H, m)<br>IR ν neat cm⁻¹: 1700 |
| 43 | H | Cl | 3-F | 3,4-trans | NMR(400MHz, CDCl₃)δppm: 0.97(3H, t, J=7.3Hz), 1.51-1.60(1H, m), 1.70-1.80(1H, m), 2.38-2.49(1H, m), 3.48(1H, d, J=9.8Hz), 3.53(1H, t, J=9.3Hz), 3.97(1H, dd, J=8.3Hz, 9.3Hz), 6.95-7.04(3H, m), 7.13(1H, d, J=8.3Hz), 7.28-7.36(2H, m), 7.61(1H, d, J=8.3Hz), 7.72(1H, s)<br>IR ν KBr cm⁻¹: 1700, m.p. 88.3-90.1° C. |

TABLE 1-continued $$\text{(I)}$$

Structure: R²-substituted and R¹-substituted phenyl attached to N of a pyrrolidinone (with C=O), 3-position bears a phenyl with Xₙ substituent, 4-position bears CH₂—CH₃.

| Compound No. | R¹ | R² | Xₙ | | Physical Properties |
|---|---|---|---|---|---|
| 44 | H | Cl | 3-F | 3,4-cis | NMR(400MHz, CDCl₃)δppm: 0.88(3H, t, J=7.4Hz), 1.02-1.13(1H, m), 1.18-1.27(1H, m), 2.64-2.74(1H, m), 3.64-3.68(1H, m), 3.96-4.05 (2H, m), 6.84-7.03(3H, m), 7.13-7.39(3H, m), 7.60-7.72(2H, m)<br>IR ν neat cm⁻¹: 1700 |
| 45 | Cl | Cl | 3-F | 3,4-trans | NMR(400MHz, CDCl₃)δppm: 0.97(3H, t, J=7.3Hz), 1.50-1.60(1H, m), 1.70-1.79(1H, m), 2.41-2.47(1H, m), 3.46-3.53(2H, m), 3.93-3.97 (1H, m), 6.93-7.03(3H, m), 7.31-7.36(1H, m), 7.42(1H, d, J=8.8Hz), 7.59(1H, dd, J=2.2Hz, J=8.8Hz), 7.84(1H, d, J=2.9Hz)<br>IR ν KBr cm⁻¹: 1705, m.p. 107.0-108.0° C. |
| 46 | CH₃ | Cl | 3-F | 3,4-trans | NMR(400MHz, CDCl₃)δppm: 0.97(3H, t, J=7.3Hz), 1.50-1.58(1H, m), 1.71-1.78(1H, m), 2.35 (3H, s), 2.40-2.46(1H, m), 3.45-3.54(2H, m), 3.93-3.98(1H, m), 6.95-7.04(3H, m), 7.21 (1H, d, J=8.8Hz), 7.30-7.36(1H, m), 7.52 (1H, dd, J=2.2Hz, J=8.8Hz), 7.67(1H, d, J=2.2Hz)<br>IR ν KBr cm⁻¹: 1705, m.p. 101.9-102.8° C. |
| 47 | H | C₂H₅ | 3-F | 3,4-trans | NMR(400MHz, CDCl₃)δppm: 0.97(3H, t, J=7.3Hz), 1.25(3H, t, J=8.1Hz), 1.51-1.62(1H, m), 1.70-1.79(1H, m), 2.39-2.47(1H, m), 2.66(2H, q, J=8.1Hz), 3.47(1H, d, J=10.3Hz), 3.55-3.59(1H, m), 4.00(1H, dd, J=8.1Hz, J=9.5Hz), 6.96-7.06(4H, m), 7.25-7.36 (2H, m), 7.42(1H, dd, J=1.5Hz, J=8.1Hz), 7.58 (1H, s)<br>IR ν neat cm⁻¹: 1700 |
| 48 | CH₃ | CH₃ | 3-F | 3,4-trans | NMR(400MHz, CDCl₃)δppm: 0.96(3H, t, J=7.3Hz), 1.51-1.60(1H, m), 1.71-1.78(1H, m), 2.24 (3H, s), 2.28(3H, s), 2.38-2.44(1H, m), 3.46(1H, d, J=10.3Hz), 3.53-3.57(1H, m), 3.96 (1H, dd, J=7.3Hz, J=9.5Hz), 6.96-6.99(2H, m), 7.05(1H, d, J=7.3Hz), 7.12(1H, d, J=8.1Hz), 7.30-7.35(2H, m), 7.48(1H, d, J=2.2Hz)<br>IR ν KBr cm⁻¹: 1700, m.p. 92.6-94.1° C. |
| 49 | H | F | 3-F | 3,4-trans | NMR(400MHz, CDCl₃)δppm: 0.97(3H, t, J=7.3Hz), 1.59-1.66(1H, m), 1.72-1.77(1H, m), 2.40-2.50(1H, m), 3.48-3.56(2H, m), 4.00(1H, dd, J=7.8Hz, J=9.3Hz), 6.84-6.89(1H, m), 6.96-7.05(3H, m), 7.30-7.42(3H, m), 7.56-7.60 (1H, m)<br>IR ν KBr cm⁻¹: 1705, m.p. 59.0-60.2° C. |
| 50 | H | F | 3-CF₃ | 3,4-trans | NMR(400MHz, CDCl₃)δppm: 0.96-0.99(3H, m), 1.53-1.65(1H, m), 1.69-1.81(1H, m), 2.40-2.52(1H, m), 3.51-3.63(2H, m), 3.96-4.08 (1H, m), 6.86-6.93(1H, m), 7.29-7.70(7H, m)<br>IR ν KBr cm⁻¹: 1705, m.p. 83.2-84.1° C. |
| 51 | H | CN | 3-F | 3,4-trans | NMR(400MHz, CDCl₃)δppm: 0.98(3H, t, J=7.3Hz), 1.51-1.66(1H, m), 1.72-1.81(1H, m), 2.45-2.53(1H, m), 3.51(1H, d, J=10.3Hz), 3.55-3.59(1H, m), 4.01(1H, dd, J=7.8Hz, 9.3Hz), 6.96-7.04(3H, m), 7.32-7.36(1H, m), 7.40-7.50(2H, m), 7.98-8.02(2H, m)<br>IR ν neat cm⁻¹: 1710, 2230, n_D(19.6° C.): 1.576 |
| 52 | H | NO₂ | 3-F | 3,4-trans | NMR(400MHz, CDCl₃)δppm: 1.00(3H, t, J=7.3Hz), 1.57-1.68(1H, m), 1.74-1.82(1H, m), 2.49-2.54(1H, m), 3.53(1H, d, J=10.0Hz), 3.61-3.65(1H, m), 4.05-4.10(1H, m), 6.97-7.09 (3H, m), 7.33-7.39(1H, m), 7.55(1H, t, 8.3Hz), 8.00-8.03(1H, m), 8.27(1H, dd, J=2.0Hz, 8.3Hz), 8.39(1H, t, J=2.0Hz)<br>IR ν KBr cm⁻¹: 1705, m.p. 107.1-109.5° C |
| 53 | H | CH₃O | 3-F | 3,4-trans | NMR(400MHz, CDCl₃)δppm: 0.97(3H, t, J=7.4Hz), 1.50-1.64(1H, m), 1.72-1.80(1H, m), 2.39-2.50(1H, m), 3.48(1H, d, J=10.0Hz), 3.53-3.57(1H, m), 3.82(3H, s), 4.00(1H, dd, J=8.0Hz, J=9.6Hz), 6.72(1H, dd, J=2.2Hz, |

TABLE 1-continued (I)

[Structure: R²/R¹-substituted phenyl-N-pyrrolidinone with Xn-phenyl and CH₂—CH₃ substituents]

| Compound No. | Substituents in formula (I) | | | Physical Properties |
|---|---|---|---|---|
| | R¹ | R² | Xₙ | |
| | | | | J=8.2Hz), 6.97-7.02(2H, m), 7.05(1H, d, J=7.2Hz), 7.12(1H, dd, J=1.2Hz, J=8.0Hz), 7.25-7.36(2H, m), 7.49(1H, t, J=2.2Hz) IR ν neat cm⁻¹: 1700 |
| 54 | H | OH | 3-F 3,4-trans | NMR(400MHz, CDCl₃)δppm: 0.95(3H, t, J=7.3Hz), 1.48-1.59(1H, m), 1.65-1.79(1H, m), 2.35-2.45(1H, m), 3.50-3.56(2H, m), 4.00(1H, dd, J=8.1Hz, J=9.5Hz), 6.60(1H, dd, J=2.2Hz, J=8.1Hz), 6.85(1H, dd, J=1.5Hz, J=8.1Hz), 6.95-7.06(3H, m), 7.18(1H, t, J=8.1Hz), 7.29-7.34(1H, m), 7.64(1H, t, J=2.2Hz) IR ν KBr cm⁻¹: 1665, 3250, m.p. 116-124° C. |
| 55 | H | OH | 3-F 3,4-cis | NMR(400MHz, CDCl₃)δppm: 0.89(3H, t, J=7.3Hz), 1.02-1.12(1H, m), 1.17-1.27(1H, m), 2.64-2.74(1H, m), 3.64-3.69(1H, m), 3.97-4.04 (2H, m), 6.67-6.69(1H, m), 6.89-6.99(3H, m), 7.13-7.22(2H, m), 7.29-7.39(1H, m), 7.61 (1H, s) IR ν KBr cm⁻¹: 3180, 1670, m.p. 157-165° C. |
| 56 | H | PhO | 3-F 3,4-trans | NMR(400MHz, CDCl₃)δppm: 0.95(3H, t, J=6.7Hz), 1.50-1.62(1H, m), 1.69-1.80(1H, m), 2.38-2.49(1H, m), 3.46-3.55(2H, m), 3.98(1H, dd, J=7.8Hz, 9.0Hz), 6.80(1H, dd, J=1.6Hz, 8.0Hz), 6.95-7.11(6H, m), 7.30-7.40(5H, m), 7.47 (1H, dd, J=1.6Hz, 8.0Hz) IR ν KBr cm⁻¹: 1700 |
| 57 | H | H | 3-F 3,4-trans | NMR(400MHz, CDCl₃)δppm: 0.97(3H, t, J=7.3Hz), 1.52-1.59(1H, m), 1.72-1.79(1H, m), 2.40-2.46(1H, m), 3.49(1H, d, J=10.5Hz), 3.55-3.60(1H, m), 4.01(1H, dd, J=7.3Hz, 9.5Hz), 6.97-7.06(3H, m), 7.17(1H, t, J=7.3Hz), 7.30-7.40(3H, m), 7.66-7.68(2H, m) IR ν KBr cm⁻¹: 1700, m.p. 87.5-89.0° C. |
| 58 | H | iso-Pr | 3-F 3,4-trans | NMR(400MHz, CDCl₃)δppm: 0.97(3H, t, J=7.3Hz), 1.26(6H, d, J=6.8Hz), 1.51-1.62(1H, m), 1.70-1.80(1H, m), 2.38-2.50(1H, m), 2.86-2.96(1H, m), 3.48(1H, d, J=10.4Hz), 3.58 (1H, t, J=9.2Hz), 4.01(1H, t, J=9.2Hz), 6.96-7.07(4H, m), 7.25-7.41(3H, m), 7.57-7.64 (1H, m) IR ν nujol cm⁻¹: 1695, m.p. 58.5-60.0° C. |
| 59 | H | iso-Pr | 3,5-F₂ 3,4-trans | NMR(400MHz, CDCl₃)δppm: 0.98(3H, t, J=7.3Hz), 1.26(6H, d, J=6.8Hz), 1.51-1.58(1H, m), 1.70-1.77(1H, m), 2.37-2.42(1H, m), 2.89-2.94(1H, m), 3.44(1H, d, J=10.3Hz), 3.58(1H, t, J=8.8Hz), 3.98(1H, t, J=8.8Jz), 6.89-7.39(6H, m), 7.55-7.64(1H, m) IR ν neat cm⁻¹: 1699 |
| 60 | H | iso-Pr | 3,4-F₂ 3,4-trans | NMR(400MHz, CDCl₃)δppm: 0.98(3H, t, J=7.3Hz), 1.26(6H, d, J=6.6Hz), 1.53-1.60(1H, m), 1.72-1.77(1H, m), 2.40-2.44(1H, m), 2.89-2.96 (1H, m), 3.47(1H, d, J=10.3Hz), 3.58(1H, t, J=9.2Hz), 3.99(1H, t, J=9.2Hz), 6.72-6.85 (3H, m), 7.04-7.55(3H, m), 7.61-7.63(1H, m) IR ν nujol cm⁻¹: 1687, m.p. 77.0-79.0° C. |
| 61 | H | iso-Pr | 3-Cl 3,4-trans | NMR(400MHz, CDCl3)δppm: 0.97(3H, t, J=7.6Hz), 1.26(6H, d, J=6.6Hz), 1.50-1.61(1H, m), 1.71-1.78(1H, m), 2.41-2.50(1H, m), 2.92(1H, sept, J=6.6Hz), 3.46(1H, d, J=10.3Hz), 3.58(1H, t, J=9.2Hz), 4.11(1H, t, J=9.2Hz), 7.05(1H, d, J=8.0Hz), 7.16(1H, d, J=7.3Hz), 7.22-7.41 (5H, m), 7.64(1H, d, J=2.2Hz) IR ν nujol cm⁻¹: 1704, m.p. 88.5-90.0° C. |
| 62 | H | iso-Pr | 3-Br 3,4-trans | NMR(400MHz, CDCl₃)δppm: 0.97(3H, t, J=7.6Hz), 1.26(6H, d, J=6.6Hz), 1.52-1.59(1H, m), 1.71-1.76(1H, m), 2.38-2.50(1H, m), 2.89-2.94 (1H, m), 3.45(1H, d, J=10.3Hz), 3.57(1H, dd, J=8.8Hz, 9.5Hz), 4.00(1H, dd, J=8.1Hz, 8.89Hz), 7.04(1H, d, J=7.3Hz), 7.15-7.43 (6H, m), 7.64(1H, s) |

TABLE 1-continued

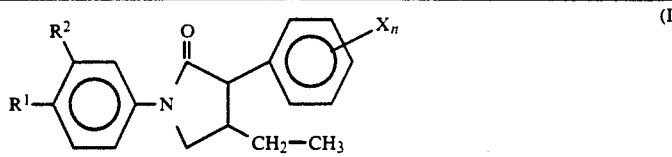

(I)

| Compound No. | Substituents in formula (I) | | | Physical Properties |
|---|---|---|---|---|
| | $R^1$ | $R^2$ | $X_n$ | |
| | | | | IR $\nu$ KBr cm$^{-1}$: 1700, m.p. 8.20–83.2° C. |

Formulation Examples and Tests

Next, formulation examples and herbicidal activity tests of certain herbicides according to the present invention will be described.

FORMULATION EXAMPLE 1

Wettable Powder

A wettable powder was obtained by sufficiently grinding and mixing 20 parts by weight of Compound No. 58 of the present invention, 2 parts by weight of Neopelex (trade name, made by Kao Corporation; sodium dodecyl benzene sulfonate), 1 part by weight of Neugen EA80 (trade name, made by Sanyo Chemical Industries, Ltd.; polyoxyethylene nonylphenyl ether), 5 parts by weight of white carbon and 72 parts by weight of diatomaceous earth.

FORMULATION EXAMPLE 2

Wettable Powder

A wettable powder was obtained by sufficiently grinding and mixing 20 parts by weight of Compound No. 59 of the present invention, 2 parts by weight of sodium alkylbenzenesulfonate, 1 part by weight of a polyoxyethylene alkylphenyl ether and 77 parts by weight of Giecrite.

FORMULATION EXAMPLE 3

Wettable Powder

A wettable powder was obtained by thoroughly grinding and mixing 50 parts by weight of Compound No. 60 of the present invention, 5 parts by weight of white carbon, 6 parts by weight of polyoxyethylene alkylphenyl ether ammonium sulfate, 2 parts by weight sodium lignine sulfonate and 37 parts by weight of diatomaceous earth by the use of a jet-O-mizer.

FORMULATION EXAMPLE 4

Flowable Formulation

A flowable formulation was obtained by adding 91.7 parts by weight of water to 5 parts by weight of Compound No. 58 of the present invention, 2 parts by weight of sodium lignine sulfonate, 0.3 part by weight of xanthane gum and 1 part by weight of a polyoxyethylene alkylaryl ether, mixing them, and then finely grinding the mixture by the use of a sand grinder.

FORMULATION EXAMPLE 5

Flowable Formulation

A flowable formulation was obtained by wet grinding and mixing 30 parts by weight of Compound No. 59 of the present invention and a solution of 10 parts by weight of Sun Ekisu P252 (trade name, as described above) in 50 parts by weight of water, and then adding a solution of 0.2 part by weight of Kelzan S (trade name, made by Kelco Corp.; xanthan gum) in 9.6 parts by weight of water and 0.2 part by weight of Deltop (trade name, made by Takeda Chemical Industries, Ltd.; organic iodine fungicide).

FORMULATION EXAMPLE 6

Powder

A powder was obtained by thoroughly grinding and mixing 1 part by weight of Compound No. 60 of the present invention, 0.5 part by weight of Emulgen 910 (trade name, made by Kao Corporation; polyoxyethylene nonylphenyl ether) and 98.5 parts by weight of kaolin clay.

FORMULATION EXAMPLE 7

Powder

A powder was obtained by mixing and grinding 3 parts by weight of Compound No. 61 of the present invention, 3 parts by weight of sodium lignine sulfonate, 2 parts by weight of a polyoxyethylene alkylaryl ether and 92 parts by weight of clay.

FORMULATION EXAMPLE 8

Dry flowable formulation

A dry flowable formulation was obtained by mixing 60 parts by weight of finely ground Compound No. 60 of the present invention, 5 parts by weight of a sodium alkylbenzenesulfonate and 35 parts by weight of a polypropylene glycol polyethylene glycol ether.

FORMULATION EXAMPLE 9

Granules 0.3 part by weight of Compound No. 58 of the present invention, 2 parts by weight of Neopelex (trade name, as described above), 2 parts by weight of Sun Ekisu P252 (trade name, made by Sanyo-Kokusaku Pulp Co., Ltd.; sodium lignine sulfonate), 72.7 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30°–60° C. in air and then crushed into granules, the granules were then classified by a sifting machine to collect granules of 0.3–2 mm.

FORMULATION EXAMPLE 10

Granules 0.5 part by weight of Compound No. 61 of the present invention, 2 parts by weight of Gosenol GL-05s (PVA made by Nippon Synthetic Chemical Industry Co., Ltd.), 2 parts of Sun Ekisu P252 (trade name, made by Sanyo-Kokusaku Pulp Co., Ltd.; sodium benzenesulfonate) and 95.5 parts of clay were thoroughly mixed, and a suitable amount of water was then added to the mixture to wet the same, followed by extrusion of the mass through an injection molding machine into pellets. After the pellets were dried at 60°-90° C. in air and then crushed into granules, the granules were then classified by a sifting machine to collect granules of 0.3-1 mm.

FORMULATION EXAMPLE 11

Emulsion

An emulsion was obtained by mutually mixing and then dissolving 10 parts by weight of Compound No. 60 of the present invention, 10 parts by weight of Sorpole 800A (trade name, made by Toho Chemical Industries Co., Ltd.; a nonionic/anionic surfactant mixture) and 80 parts by weight of o-xylene.

Test 1 Treatment of Soil under Submerged Condition

Pre-emergence Treatment

1/5000-are Wagner pots were filled with soil Seeds or tubers of *Echinochloa crusgalli*, bulrush (*Scirpus juncoides*), *Sagittaria pygmaea*, monochoria (*Monochoria vaginalis*), water nutgrass (*Cyperus serotinus*) and false pimpernel (*Lindernia pyxidaria*) were sown or planted under submerged condition. Two pairs of rice (*Oryza sativa*) seedlings (2-3 leaf stage), which had been reared in advance, were transplanted to each pot and were allowed to grow in a green house. Each pair consisted of two rice seedlings. One day later (before emergence of weeds), each pot was treated with granules which had been prepared by processing a predetermined amount of the test compound in accordance with the procedure described in Formulation Example 9. The growing state of weeds and the injurious state to rice were observed 30 days later. The results are summarized in Tables 2 and 3.

In the tables, the damage degree of each test plant and the injurious degree to rice were determined by comparing the growing state of the test plant and rice with that of the corresponding plant and rice in untreated pots, and they are denoted in accordance with the following standard.

| Rank | Growth rate (%) expressed in terms of the perentage of dry weight relative to the dry weight of untreated group | |
|---|---|---|
| 5 | 0-5 | (Death) |
| 4 | 6-10 | (Severe damages) |
| 3 | 11-40 | (Medium damages) |
| 2 | 41-70 | (Small damages) |
| 1 | 71-90 | (Slight damages) |
| 0 | 91-100 | (No damages) |

Comparative Compounds A, B, C., D and E mean the following compounds, respectively.

A: 1-(3-trifluoromethylphenyl)-3-chloro-4-chloromethylpyrrolidin-2-one.

B: 1-methyl-3-phenyl-5-(3-trifluoromethylphenyl)-pyridin-4(1H)-one.

C: 4-chloromethyl-3-(3-chlorophenyl)-1-(3-trifluoromethylphenyl)pyrrolidin-2-one.

D: 4-ethyl-3-(3-fluorophenyl)-1-(3-trifluoromethylphenyl)pyrrolidin-2-one.

E: 3,4-cis-4-ethyl-3-(3-chlorophenyl)-1-(3-isopropylphenyl)pyrrolidin-2-one (which was prepared in Reference Example 7).

TABLE 2

| Compound No. | Application rate, kg/ha | *Echinochloa crusgalli* | Monochoria (*Monochoria vaginalis*) | Bulrush (*Scirpus juncoides*) | *Sagittaria pygmaea* | Water nutgrass (*Cyperus serotinus*) | Rice (*Oryza sativa*) |
|---|---|---|---|---|---|---|---|
| 1 | 0.1 | 5 | 5 | 4 | 3 | 4 | 0 |
|   | 0.2 | 5 | 5 | 4 | 4 | 5 | 0 |
|   | 0.4 | 5 | 5 | 5 | 5 | 5 | 0 |
| 2 | 0.1 | 3 | 2 | 2 | 2 | 2 | 0 |
|   | 0.2 | 4 | 4 | 3 | 3 | 3 | 0 |
|   | 0.4 | 5 | 5 | 4 | 4 | 4 | 0 |
| 3 | 0.1 | 5 | 5 | 4 | 3 | 4 | 0 |
|   | 0.2 | 5 | 5 | 5 | 4 | 5 | 0 |
|   | 0.4 | 5 | 5 | 5 | 5 | 5 | 0 |
| 4 | 0.1 | 2 | 2 | 2 | 2 | 2 | 0 |
|   | 0.2 | 4 | 3 | 3 | 3 | 3 | 0 |
|   | 0.4 | 5 | 4 | 4 | 4 | 4 | 0 |
| 5 | 0.1 | 5 | 5 | 4 | 3 | 5 | 0 |
|   | 0.2 | 5 | 5 | 5 | 4 | 5 | 0 |
|   | 0.4 | 5 | 5 | 5 | 5 | 5 | 1 |
| 6 | 0.1 | 2 | 2 | 1 | 1 | 2 | 0 |
|   | 0.2 | 4 | 3 | 3 | 2 | 3 | 0 |
|   | 0.4 | 5 | 5 | 4 | 4 | 4 | 0 |
| 7 | 0.1 | 5 | 5 | 3 | 3 | 4 | 0 |
|   | 0.2 | 5 | 5 | 4 | 4 | 5 | 0 |
|   | 0.4 | 5 | 5 | 5 | 5 | 5 | 2 |
| 8 | 0.1 | 3 | 2 | 1 | 2 | 2 | 0 |
|   | 0.2 | 4 | 4 | 3 | 3 | 3 | 0 |
|   | 0.4 | 5 | 5 | 4 | 4 | 4 | 0 |
| 9 | 0.1 | 5 | 5 | 4 | 3 | 3 | 0 |
|   | 0.2 | 5 | 5 | 5 | 4 | 4 | 0 |
|   | 0.4 | 5 | 5 | 5 | 5 | 5 | 0 |
| 10 | 0.1 | 2 | 2 | 2 | 2 | 1 | 0 |
|   | 0.2 | 4 | 3 | 3 | 2 | 3 | 0 |
|   | 0.4 | 5 | 4 | 4 | 4 | 4 | 0 |
| 11 | 0.1 | 5 | 5 | 3 | 4 | 4 | 0 |
|   | 0.2 | 5 | 5 | 4 | 5 | 5 | 0 |
|   | 0.4 | 5 | 5 | 5 | 5 | 5 | 1 |
| 12 | 0.1 | 2 | 2 | 2 | 1 | 2 | 0 |
|   | 0.2 | 4 | 3 | 3 | 2 | 3 | 0 |

TABLE 2-continued

| Compound No. | Application rate. kg/ha | Echinochloa crusgalli | Monochoria (Monochoria vaginalis) | Bulrush (Scirpus juncoides) | Sagittaria pygmaea | Water nutgrass (Cyperus serotinus) | Rice (Oryza sativa) |
|---|---|---|---|---|---|---|---|
| | 0.4 | 5 | 4 | 4 | 4 | 4 | 0 |
| 13 | 0.1 | 5 | 5 | 4 | 3 | 5 | 0 |
| | 0.2 | 5 | 5 | 5 | 5 | 5 | 0 |
| | 0.4 | 5 | 5 | 5 | 5 | 5 | 1 |
| 14 | 0.1 | 1 | 1 | 1 | 1 | 2 | 0 |
| | 0.2 | 3 | 3 | 3 | 2 | 3 | 0 |
| | 0.4 | 4 | 5 | 4 | 4 | 4 | 0 |
| 15 | 0.1 | 5 | 5 | 3 | 3 | 4 | 0 |
| | 0.2 | 5 | 5 | 5 | 4 | 5 | 0 |
| | 0.4 | 5 | 5 | 5 | 5 | 5 | 1 |
| 16 | 0.1 | 1 | 1 | 1 | 1 | 1 | 0 |
| | 0.2 | 2 | 3 | 3 | 3 | 3 | 0 |
| | 0.4 | 5 | 5 | 4 | 4 | 4 | 0 |
| 17 | 0.1 | 5 | 5 | 4 | 3 | 3 | 0 |
| | 0.2 | 5 | 5 | 5 | 4 | 5 | 0 |
| | 0.4 | 5 | 5 | 5 | 5 | 5 | 1 |
| 18 | 0.1 | 2 | 2 | 1 | 1 | 2 | 0 |
| | 0.2 | 4 | 4 | 3 | 3 | 4 | 0 |
| | 0.4 | 5 | 5 | 4 | 4 | 5 | 0 |
| 19 | 0.1 | 4 | 3 | 2 | 2 | 3 | 0 |
| | 0.2 | 5 | 4 | 3 | 3 | 4 | 0 |
| | 0.4 | 5 | 5 | 4 | 4 | 5 | 0 |
| 20 | 0.1 | 2 | 1 | 1 | 1 | 2 | 0 |
| | 0.2 | 3 | 3 | 2 | 2 | 3 | 0 |
| | 0.4 | 4 | 4 | 3 | 3 | 4 | 0 |
| 21 | 0.1 | 4 | 3 | 2 | 2 | 3 | 0 |
| | 0.2 | 5 | 4 | 4 | 3 | 4 | 0 |
| | 0.4 | 5 | 5 | 4 | 4 | 5 | 0 |
| 22 | 0.1 | 2 | 1 | 1 | 1 | 2 | 0 |
| | 0.2 | 3 | 3 | 2 | 2 | 3 | 0 |
| | 0.4 | 5 | 4 | 4 | 4 | 3 | 0 |
| 23 | 0.1 | 4 | 2 | 2 | 3 | 4 | 0 |
| | 0.2 | 5 | 4 | 4 | 4 | 5 | 0 |
| | 0.4 | 5 | 5 | 5 | 5 | 5 | 1 |
| 24 | 0.1 | 2 | 1 | 1 | 1 | 2 | 0 |
| | 0.2 | 3 | 3 | 2 | 3 | 3 | 0 |
| | 0.4 | 5 | 4 | 4 | 3 | 4 | 0 |
| 25 | 0.1 | 5 | 5 | 4 | 4 | 3 | 0 |
| | 0.2 | 5 | 5 | 5 | 5 | 5 | 0 |
| | 0.4 | 5 | 5 | 5 | 5 | 5 | 0 |
| 26 | 0.1 | 2 | 1 | 2 | 2 | 2 | 0 |
| | 0.2 | 3 | 3 | 3 | 3 | 3 | 0 |
| | 0.4 | 5 | 4 | 4 | 4 | 4 | 0 |
| 27 | 0.1 | 4 | 3 | 3 | 2 | 3 | 0 |
| | 0.2 | 5 | 4 | 4 | 3 | 4 | 0 |
| | 0.4 | 5 | 5 | 5 | 4 | 5 | 0 |
| 28 | 0.1 | 2 | 1 | 1 | 1 | 2 | 0 |
| | 0.2 | 3 | 3 | 3 | 2 | 4 | 0 |
| | 0.4 | 5 | 4 | 4 | 4 | 4 | 0 |
| 29 | 0.1 | 5 | 5 | 4 | 3 | 4 | 0 |
| | 0.2 | 5 | 5 | 5 | 4 | 5 | 0 |
| | 0.4 | 5 | 5 | 5 | 5 | 5 | 1 |
| 30 | 0.1 | 2 | 2 | 1 | 2 | 2 | 0 |
| | 0.2 | 3 | 3 | 3 | 3 | 3 | 0 |
| | 0.4 | 4 | 4 | 4 | 4 | 4 | 0 |
| 31 | 0.1 | 5 | 5 | 4 | 3 | 4 | 0 |
| | 0.2 | 5 | 5 | 5 | 4 | 5 | 0 |
| | 0.4 | 5 | 5 | 5 | 5 | 5 | 1 |
| 32 | 0.1 | 2 | 1 | 1 | 1 | 2 | 0 |
| | 0.2 | 4 | 3 | 3 | 2 | 3 | 0 |
| | 0.4 | 5 | 4 | 4 | 3 | 4 | 0 |
| 33 | 0.1 | 5 | 4 | 3 | 3 | 3 | 0 |
| | 0.2 | 5 | 5 | 4 | 4 | 4 | 0 |
| | 0.4 | 5 | 5 | 5 | 5 | 5 | 1 |
| 34 | 0.1 | 2 | 1 | 1 | 1 | 0 | 0 |
| | 0.2 | 3 | 2 | 3 | 2 | 2 | 0 |
| | 0.4 | 4 | 3 | 4 | 3 | 3 | 0 |
| 35 | 0.1 | 5 | 5 | 4 | 4 | 5 | 0 |
| | 0.2 | 5 | 5 | 5 | 4 | 5 | 0 |
| | 0.4 | 5 | 5 | 5 | 5 | 5 | 0 |
| 36 | 0.1 | 5 | 5 | 4 | 3 | 4 | 0 |
| | 0.2 | 5 | 5 | 5 | 5 | 5 | 0 |
| | 0.4 | 5 | 5 | 5 | 5 | 5 | 1 |
| 37 | 0.1 | 5 | 5 | 3 | 2 | 3 | 0 |
| | 0.2 | 5 | 5 | 4 | 3 | 4 | 0 |
| | 0.4 | 5 | 5 | 5 | 4 | 5 | 0 |
| 38 | 0.1 | 5 | 5 | 4 | 3 | 4 | 0 |
| | 0.2 | 5 | 5 | 5 | 4 | 5 | 0 |

TABLE 2-continued

| Compound No. | Application rate, kg/ha | Echinochloa crusgalli | Monochoria (Monochoria vaginalis) | Bulrush (Scirpus juncoides) | Sagittaria pygmaea | Water nutgrass (Cyperus serotinus) | Rice (Oryza sativa) |
|---|---|---|---|---|---|---|---|
|  | 0.4 | 5 | 5 | 5 | 5 | 5 | 1 |
| 39 | 0.1 | 5 | 5 | 3 | 3 | 2 | 0 |
|  | 0.2 | 5 | 5 | 4 | 4 | 3 | 0 |
|  | 0.4 | 5 | 5 | 5 | 5 | 5 | 0 |
| 40 | 0.1 | 5 | 5 | 4 | 3 | 3 | 0 |
|  | 0.2 | 5 | 5 | 5 | 4 | 4 | 0 |
|  | 0.4 | 5 | 5 | 5 | 5 | 5 | 1 |
| 41 | 0.1 | 5 | 5 | 5 | 4 | 3 | 0 |
|  | 0.2 | 5 | 5 | 5 | 5 | 4 | 0 |
|  | 0.4 | 5 | 5 | 5 | 5 | 5 | 0 |
| 42 | 0.1 | 2 | 3 | 2 | 1 | 0 | 0 |
|  | 0.2 | 3 | 4 | 3 | 3 | 2 | 0 |
|  | 0.4 | 4 | 4 | 4 | 4 | 3 | 0 |
| 43 | 0.1 | 5 | 5 | 5 | 4 | 3 | 0 |
|  | 0.2 | 5 | 5 | 5 | 5 | 5 | 0 |
|  | 0.4 | 5 | 5 | 5 | 5 | 5 | 1 |
| 44 | 0.1 | 3 | 3 | 3 | 2 | 1 | 0 |
|  | 0.2 | 4 | 4 | 4 | 3 | 3 | 0 |
|  | 0.4 | 4 | 5 | 4 | 4 | 4 | 0 |
| 45 | 0.1 | 4 | 4 | 4 | 3 | 3 | 0 |
|  | 0.2 | 4 | 5 | 4 | 4 | 4 | 0 |
|  | 0.4 | 5 | 5 | 5 | 4 | 4 | 0 |
| 46 | 0.1 | 4 | 5 | 4 | 3 | 3 | 0 |
|  | 0.2 | 5 | 5 | 5 | 4 | 4 | 0 |
|  | 0.4 | 5 | 5 | 5 | 5 | 5 | 0 |
| 47 | 0.1 | 4 | 4 | 4 | 3 | 2 | 0 |
|  | 0.2 | 4 | 5 | 4 | 4 | 3 | 0 |
|  | 0.4 | 5 | 5 | 5 | 4 | 4 | 0 |
| 48 | 0.1 | 4 | 4 | 4 | 3 | 3 | 0 |
|  | 0.2 | 5 | 5 | 5 | 4 | 4 | 0 |
|  | 0.4 | 5 | 5 | 5 | 5 | 4 | 0 |
| 49 | 0.1 | 5 | 5 | 4 | 3 | 3 | 0 |
|  | 0.2 | 5 | 5 | 5 | 4 | 4 | 0 |
|  | 0.4 | 5 | 5 | 5 | 4 | 4 | 0 |
| 50 | 0.1 | 2 | 3 | 1 | 1 | 2 | 0 |
|  | 0.2 | 3 | 3 | 3 | 3 | 3 | 0 |
|  | 0.4 | 4 | 4 | 5 | 4 | 4 | 0 |
| 51 | 0.1 | 4 | 4 | 4 | 3 | 2 | 0 |
|  | 0.2 | 4 | 5 | 4 | 4 | 3 | 0 |
|  | 0.4 | 5 | 5 | 5 | 4 | 3 | 0 |
| 52 | 0.1 | 4 | 4 | 4 | 2 | 2 | 0 |
|  | 0.2 | 4 | 5 | 4 | 3 | 3 | 0 |
|  | 0.4 | 5 | 5 | 5 | 4 | 3 | 0 |
| 53 | 0.1 | 4 | 4 | 3 | 3 | 2 | 0 |
|  | 0.2 | 4 | 5 | 4 | 4 | 3 | 0 |
|  | 0.4 | 5 | 5 | 5 | 4 | 4 | 0 |
| 54 | 0.1 | 2 | 3 | 3 | 2 | 2 | 0 |
|  | 0.2 | 3 | 4 | 4 | 3 | 3 | 0 |
|  | 0.4 | 5 | 5 | 4 | 4 | 4 | 0 |
| 55 | 0.1 | 1 | 2 | 1 | 1 | 1 | 0 |
|  | 0.2 | 2 | 3 | 2 | 2 | 2 | 0 |
|  | 0.4 | 4 | 4 | 3 | 3 | 3 | 0 |
| 56 | 0.1 | 4 | 4 | 3 | 3 | 3 | 0 |
|  | 0.2 | 5 | 5 | 4 | 4 | 4 | 0 |
|  | 0.4 | 5 | 5 | 5 | 5 | 4 | 0 |
| 57 | 0.1 | 3 | 4 | 2 | 2 | 3 | 0 |
|  | 0.2 | 4 | 4 | 3 | 3 | 4 | 0 |
|  | 0.4 | 5 | 5 | 4 | 4 | 4 | 0 |
| A | 0.1 | 2 | 3 | 2 | 1 | 2 | 2 |
|  | 0.2 | 3 | 4 | 3 | 3 | 3 | 3 |
|  | 0.4 | 5 | 5 | 4 | 4 | 5 | 5 |
| B | 0.1 | 3 | 3 | 3 | 3 | 2 | 2 |
|  | 0.2 | 4 | 4 | 4 | 4 | 3 | 4 |
|  | 0.4 | 5 | 5 | 5 | 4 | 4 | 5 |

TABLE 3

Treatment of Soil under Submerged Condition (Pre-emergence Treatment)

| Compound No. | Application rate, kg/ha | Echinochloa crusgalli | Monochoria (Monochoria vaginalis) | Bulrush (Scirpus juncoides) | False pimpernel (Lindernia pyxidaria) | Rice (Oryza sativa) |
|---|---|---|---|---|---|---|
| 58 | 0.03 | 5 | 5 | 3 | 5 | 0 |
|  | 0.05 | 5 | 5 | 4 | 5 | 0 |
|  | 0.1 | 5 | 5 | 5 | 5 | 1 |

TABLE 3-continued

| | | Treatment of Soil under Submerged Condition (Pre-emergence Treatment) | | | | |
|---|---|---|---|---|---|---|
| Compound No. | Application rate, kg/ha | Echinochloa crusgalli | Monochoria (Monochoria vaginalis) | Bulrush (Scirpus juncoides) | False pimpernel (Lindernia pyxidaria) | Rice (Oryza sativa) |
| 59 | 0.03 | 5 | 5 | 3 | 5 | 0 |
| | 0.05 | 5 | 5 | 4 | 5 | 0 |
| | 0.1 | 5 | 5 | 5 | 5 | 1 |
| 60 | 0.03 | 5 | 4 | 2 | 5 | 0 |
| | 0.05 | 5 | 5 | 3 | 5 | 0 |
| | 0.1 | 5 | 5 | 5 | 5 | 0 |
| 61 | 0.03 | 5 | 3 | 2 | 5 | 0 |
| | 0.05 | 5 | 4 | 3 | 5 | 0 |
| | 0.1 | 5 | 5 | 5 | 5 | 0 |
| 62 | 0.03 | 5 | 3 | 2 | 5 | 0 |
| | 0.05 | 5 | 4 | 4 | 5 | 0 |
| | 0.1 | 5 | 5 | 5 | 5 | 0 |
| A | 0.03 | 0 | 0 | 0 | 0 | 0 |
| | 0.05 | 1 | 1 | 1 | 2 | 1 |
| | 0.1 | 2 | 3 | 2 | 3 | 2 |
| C | 0.03 | 0 | 0 | 0 | 0 | 0 |
| | 0.05 | 3 | 2 | 1 | 2 | 0 |
| | 0.1 | 5 | 5 | 4 | 4 | 0 |
| D | 0.03 | 2 | 1 | 0 | 1 | 0 |
| | 0.05 | 3 | 3 | 2 | 3 | 0 |
| | 0.1 | 5 | 5 | 4 | 5 | 0 |
| E | 0.03 | 0 | 0 | 0 | 0 | 0 |
| | 0.05 | 0 | 0 | 0 | 0 | 0 |
| | 0.1 | 2 | 1 | 0 | 1 | 0 |

In these tests, as compared with Comparative Agents A, C and D, the herbicidal compositions regarding the present invention exerted higher herbicidal effects to the sample weeds in the paddy fields in spite of the low application rates, and they also exerted excellent safety to the rice. In addition, the cis isomer (Comparative Agent E) corresponding to the compound of the present invention scarcely exhibited the herbicidal effect.

Test 2 Treatment of Soil under Submerged Condition

Growing Period Treatment

1/5000-are Wagner pots were filled with soil. Seeds of Echinochloa crusgalli, bulrush (Scirpus juncoides), monochoria (Monochoria vaginalis) and false pimpernel (Lindernia pyxidaria) were sown under submerged condition. Two pairs of rice (Oryza sativa) seedlings (2-3 leaf stage), which had been reared in advance, were transplanted to each pot and were allowed to grow in a green house. Each pair consisted of two rice seedlings. When barnyard grass became bifoliate, each pot was treated with granules which had been prepared by processing a predetermined amount of the test compound in accordance with the procedure described in Formulation Example 10. The emergence state of weeds and the injurious state to rice were observed 30 days later. The results are summarized in Table 4. In the table, the damage degree of each test plant and the injurious degree to rice were determined in the same manner as in Test 1.

TABLE 4

| | | Treatment of Soil under Submerged Condition (Growing Period Treatment) | | | | |
|---|---|---|---|---|---|---|
| Compound No. | Application rate, kg/ha | Echinochloa crusgalli | Monochoria (Monochoria vaginalis) | Bulrush (Scirpus juncoides) | False pimpernel (Lindernia pyxidaria) | Rice (Oryza sativa) |
| 58 | 0.13 | 5 | 4 | 2 | 5 | 0 |
| | 0.25 | 5 | 5 | 4 | 5 | 0 |
| | 0.5 | 5 | 5 | 5 | 5 | 1 |
| 59 | 0.13 | 5 | 4 | 3 | 5 | 0 |
| | 0.25 | 5 | 5 | 4 | 5 | 0 |
| | 0.5 | 5 | 5 | 5 | 5 | 1 |
| 60 | 0.13 | 5 | 4 | 2 | 4 | 0 |
| | 0.25 | 5 | 5 | 3 | 5 | 0 |
| | 0.5 | 5 | 5 | 5 | 5 | 1 |
| 61 | 0.13 | 4 | 3 | 2 | 5 | 0 |
| | 0.25 | 5 | 4 | 3 | 5 | 0 |
| | 0.5 | 5 | 5 | 5 | 5 | 0 |
| 62 | 0.13 | 4 | 3 | 2 | 4 | 0 |
| | 0.25 | 5 | 4 | 3 | 5 | 0 |
| | 0.5 | 5 | 5 | 4 | 5 | 0 |
| A | 0.13 | 0 | 0 | 0 | 0 | 0 |
| | 0.25 | 1 | 1 | 0 | 2 | 2 |
| | 0.5 | 2 | 2 | 1 | 2 | 3 |
| C | 0.13 | 0 | 0 | 0 | 0 | 0 |
| | 0.25 | 2 | 1 | 1 | 1 | 0 |
| | 0.5 | 3 | 2 | 2 | 3 | 0 |
| D | 0.13 | 2 | 1 | 0 | 1 | 0 |

TABLE 4-continued

Treatment of Soil under Submerged Condition
(Growing Period Treatment)

| Compound No. | Application rate, kg/ha | Echinochloa crusgalli | Monochoria (Monochoria vaginalis) | Bulrush (Scirpus juncoides) | False pimpernel (Lindernia pyxidaria) | Rice (Oryza sativa) |
|---|---|---|---|---|---|---|
|   | 0.25 | 3 | 3 | 1 | 3 | 0 |
|   | 0.5  | 5 | 5 | 3 | 5 | 0 |
| E | 0.13 | 0 | 0 | 0 | 0 | 0 |
|   | 0.25 | 0 | 0 | 0 | 0 | 0 |
|   | 0.5  | 1 | 1 | 0 | 1 | 0 |

Similarly in these tests, as compared with Comparative Agents A, C and D, the herbicidal compositions regarding the present invention exerted higher herbicidal effects to the sample weeds in the paddy fields in spite of the low application rates, and they also exerted excellent safety to the rice. In addition, the cis isomer (Comparative Agent E) corresponding to the compound of the present invention scarcely exhibited the herbicidal effect.

What is claimed is:

1. A method for preparing a 3,4-trans isomer of 4-ethyl-1-(substituted phenyl)-3-(substituted phenyl)pyrrolidin-2-ones represented by the formula (I)

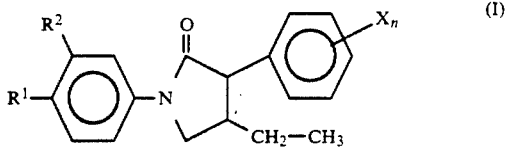

(wherein $R^1$ is a hydrogen atom, halogen atom or methyl group; $R^2$ is a trifluoromethyl group, haloalkoxy group having 1 to 3 carbon atoms, haloalkylthio group having 1 to 3 carbon atoms, lower alkyl group having 1 to 4 carbon atoms, alkoxy group having 1 to 4 carbon atoms, nitro group, cyano group, phenoxy group, hydroxyl group or halogen atom; X is a hydrogen atom, halogen atom, trifluoromethyl group, alkyl group having 1 to 3 carbon atoms, cyano group or nitro group; and n is 1 or 2 and denotes the number of the substituents represented by X, and in the case of n=2, the groups of X may be identical or different which comprises the step of reacting a base with a 3,4-cis isomer of the 4-ethyl-1-(substituted phenyl)-3-(substituted phenyl)pyrrolidin-2-ones represented by the formula (I).

2. The method according to claim 1 wherein the 3,4-cis isomer of the 4-ethyl-1-(substituted phenyl)-3-(substituted phenyl)pyrrolidin-2-ones is included in a mixture with the 3,4-trans isomer of the 4-ethyl-1-(substituted phenyl)-3-(substituted phenyl)pyrrolidin-2-ones.

3. A 3,4-trans isomer of 4-ethyl-1-(substituted phenyl)-3-(substituted phenyl)pyrrolidin-2-ones represented by the formula (III)

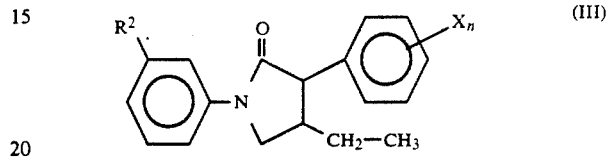

wherein $R^2$ is an isopropyl group, and X is a fluorine atom, chlorine atom or bromine atom substituted at the 3-position, or fluorine atoms substituted at the 3- and 4-positions or the 3- and 5-positions.

4. A herbicidal composition for paddy fields which contains, as a herbicidally active ingredient, a 3,4-trans isomer of 4-ethyl-1-(substituted phenyl)-3-(substituted phenyl)pyrrolidin-2-ones of claim 3.

5. A method of controlling weeds in a rice paddy field without harming the rice plant which comprises applying to the rice paddy field an effective amount of the compound of claim 3.

6. A 3,4-trans isomer according to claim 3, substantially free from the cis isomer.

7. A 3,4-trans isomer according to claim 3, wherein $X_n$ is 3-F.

8. A 3,4-trans isomer according to claim 3, wherein $X_n$ is $3,5F_2$.

9. A 3,4-trans isomer according to claim 3, wherein $X_n$ is $3,4-F_2$.

10. A 3,4-trans isomer according to claim 3, wherein $X_n$ is 3-Cl.

11. A 3,4-trans isomer according to claim 3, wherein $X_n$ is 3Br.

12. A herbicidal composition according to claim 4, wherein $X_n$ is 3-F.

13. A herbicidal composition according to claim 4, wherein $X_n$ is $3,5-F_2$.

14. A herbicidal composition according to claim 4, wherein $X_n$ is $3,4F_2$.

15. A herbicidal composition according to claim 4, wherein $X_n$ is 3-Cl.

16. A herbicidal composition according to claim 4, wherein $X_n$ is 3-Br.

17. A method according to claim 5, wherein $X_n$ is $3,5-F_2$.

18. A method according to claim 5, wherein $X_n$ is $3,4-F_2$.

19. A method according to claim 5, wherein $X_n$ is 3-Cl.

20. A method according to claim 5, wherein $X_n$ is 3-Br.

* * * * *